US012728285B2

(12) United States Patent
Sjolund et al.

(10) Patent No.: US 12,728,285 B2
(45) Date of Patent: Sep. 8, 2026

(54) GENERATIVE MODEL OF PHASE SPACE

(71) Applicant: Elekta AB (publ), Stockholm (SE)

(72) Inventors: Jens Olof Sjolund, Uppsala (SE); Carl Axel Håkan Nordström, Stockholm (SE)

(73) Assignee: Elekta AB (publ), Stockholm (SE)

( * ) Notice: Subject to any disclaimer, the term of this patent is extended or adjusted under 35 U.S.C. 154(b) by 184 days.

(21) Appl. No.: 18/689,175

(22) PCT Filed: Sep. 16, 2021

(86) PCT No.: PCT/EP2021/075541
§ 371 (c)(1),
(2) Date: Mar. 5, 2024

(87) PCT Pub. No.: WO2023/041167
PCT Pub. Date: Mar. 23, 2023

(65) Prior Publication Data
US 2024/0366962 A1 Nov. 7, 2024

(51) Int. Cl.
*A61N 5/10* (2006.01)
*G16H 20/40* (2018.01)
*G16H 50/50* (2018.01)

(52) U.S. Cl.
CPC ......... *A61N 5/1031* (2013.01); *A61N 5/1039* (2013.01); *A61N 5/1071* (2013.01);
(Continued)

(58) Field of Classification Search
CPC ........ A61N 5/10; A61N 5/103; A61N 5/1031; A61N 2005/1034; A61N 5/1037;
(Continued)

(56) References Cited

U.S. PATENT DOCUMENTS 6,029,079 A * 2/2000 Cox ..................... A61N 5/1031 600/407
6,285,969 B1 * 9/2001 Svatos ................. A61N 5/1031 703/2

(Continued)

FOREIGN PATENT DOCUMENTS

WO WO-2023041167 A1 3/2023

OTHER PUBLICATIONS

"International Application Serial No. PCT/EP2021/075541, International Search Report mailed Jun. 9, 22", 4 pgs.

(Continued)

*Primary Examiner* — Allen C. Ho
(74) *Attorney, Agent, or Firm* — Schwegman Lundberg & Woessner, P.A.

(57) ABSTRACT

Systems and methods are disclosed for simulating dose deposition. The systems and methods perform operations comprising: receiving a set of training data representing phase space of a radiotherapy treatment device comprising propagation and scattering of particles inside the radiotherapy treatment device; training a generative machine learning model based on the set of training data to generate one or more samples of the phase space of the radiotherapy treatment device; and simulating dose deposition at a particular region of interest based on the one or more samples of the phase space generated by the generative machine learning model.

23 Claims, 12 Drawing Sheets

(52) U.S. Cl.
CPC ........... *A61N 5/1081* (2013.01); *G16H 20/40* (2018.01); *G16H 50/50* (2018.01); *A61N 2005/1034* (2013.01); *A61N 2005/1041* (2013.01); *A61N 2005/1074* (2013.01); *A61N 2005/1087* (2013.01); *A61N 2005/1089* (2013.01)

(58) Field of Classification Search
CPC ................ A61N 5/1038; A61N 5/1039; A61N 2005/1041; A61N 5/1042; A61N 5/1045; A61N 5/1047; A61N 5/1071; A61N 2005/1072; A61N 2005/1074; A61N 5/1081; A61N 2005/1087; A61N 2005/1089
USPC .............................. 378/65; 250/492.1, 492.3
See application file for complete search history.

(56) References Cited

U.S. PATENT DOCUMENTS

| | | | | |
|---|---|---|---|---|
| 6,535,837 | B1 * | 3/2003 | Schach Von Wittenau | A61N 5/1031 378/65 |
| 6,714,620 | B2 * | 3/2004 | Caflisch | A61N 5/103 378/65 |
| 7,197,404 | B2 * | 3/2007 | Holland | A61N 5/1031 250/363.01 |
| 8,125,813 | B2 * | 2/2012 | Nizin | A61N 5/1031 250/492.1 |
| 8,401,148 | B2 * | 3/2013 | Lu | A61N 5/1031 378/65 |
| 9,370,672 | B2 * | 6/2016 | Parsai | A61N 5/1042 |
| 9,782,607 | B2 * | 10/2017 | Wiersma | A61N 5/1031 |
| 9,878,181 | B2 * | 1/2018 | Russo | A61N 5/1075 |
| 10,046,177 | B2 * | 8/2018 | Sjölund | A61N 5/1038 |
| 10,342,994 | B2 * | 7/2019 | Kuusela | A61N 5/1031 |
| 10,346,593 | B2 * | 7/2019 | Kuusela | A61N 5/1031 |
| 10,417,390 | B2 * | 9/2019 | Svatos | A61N 5/10 |
| 10,493,299 | B2 * | 12/2019 | Hissoiny | A61N 5/103 |
| 10,565,329 | B2 * | 2/2020 | Greenwood | G06F 30/20 |
| 10,672,153 | B2 * | 6/2020 | Adler | G06T 7/10 |
| 10,737,115 | B2 * | 8/2020 | Li | A61N 5/1031 |
| 10,918,888 | B2 * | 2/2021 | Ramezanzadeh Moghadam | A61N 5/1071 |
| 11,013,936 | B2 * | 5/2021 | Cordero Marcos | A61N 5/1039 |
| 11,020,615 | B2 * | 6/2021 | Eriksson | A61N 5/1031 |
| 11,056,243 | B2 * | 7/2021 | Sjölund | A61N 5/103 |
| 11,077,320 | B1 * | 8/2021 | Hibbard | A61N 5/1067 |
| 11,083,913 | B2 * | 8/2021 | Lachaine | A61N 5/1037 |
| 11,097,128 | B2 * | 8/2021 | Sjölund | A61N 5/1031 |
| 11,100,632 | B2 * | 8/2021 | Han | A61N 5/103 |
| 11,141,609 | B2 * | 10/2021 | Tilly | A61N 5/1071 |
| 11,167,152 | B2 * | 11/2021 | Liu | A61N 5/103 |
| 11,358,003 | B2 * | 6/2022 | Sjölund | A61N 5/103 |
| 11,433,258 | B2 * | 9/2022 | Maltz | A61N 5/103 |
| 11,517,768 | B2 * | 12/2022 | Hibbard | A61N 5/1031 |
| 11,557,390 | B2 * | 1/2023 | Hibbard | A61N 5/1039 |
| 11,651,848 | B2 * | 5/2023 | Kuusela | A61N 5/1031 600/1 |
| 11,679,274 | B2 * | 6/2023 | Peltola | A61N 5/1031 378/65 |
| 11,717,702 | B2 * | 8/2023 | Yuan | A61N 5/1031 600/1 |
| 11,813,479 | B2 * | 11/2023 | Czeizler | A61N 5/103 |
| 11,850,445 | B2 * | 12/2023 | Hibbard | A61N 5/1039 |
| 11,865,362 | B2 * | 1/2024 | Nguyen | A61N 5/1031 |
| 11,931,599 | B2 * | 3/2024 | Holmstrom | A61N 5/1031 |
| 11,964,170 | B2 * | 4/2024 | Li | A61N 5/1031 |
| 11,992,702 | B2 * | 5/2024 | Hibbard | A61N 5/1031 |
| 12,017,089 | B2 * | 6/2024 | Flaschner | A61N 5/1045 |
| 12,023,518 | B2 * | 7/2024 | Weese | A61N 5/1031 |
| 12,076,587 | B2 * | 9/2024 | Lansonneur | A61N 5/1031 |
| 12,121,747 | B2 * | 10/2024 | Peltola | A61N 5/1038 |
| 12,128,250 | B2 * | 10/2024 | Wu | A61N 5/1039 |
| 12,194,311 | B2 * | 1/2025 | Bai | A61N 5/1031 |
| 12,226,657 | B2 * | 2/2025 | Hibbard | A61N 5/1084 |
| 12,239,853 | B2 * | 3/2025 | Shi | A61N 5/1071 |
| 12,274,895 | B2 * | 4/2025 | Tilly | A61N 5/1071 |
| 12,370,378 | B2 * | 7/2025 | Lofman | A61N 5/1071 |
| 12,370,381 | B2 * | 7/2025 | Bose | A61N 5/1039 |
| 12,383,763 | B2 * | 8/2025 | Tang | A61N 5/1031 |
| 12,420,112 | B2 * | 9/2025 | Chen | A61N 5/1031 |
| 12,496,464 | B2 * | 12/2025 | Peri | A61N 5/1031 |
| 12,502,552 | B2 * | 12/2025 | Sjölund | A61N 5/1031 |
| 12,508,446 | B2 * | 12/2025 | Tilly | A61N 5/1067 |

OTHER PUBLICATIONS

"International Application Serial No. PCT/EP2021/075541, Written Opinion mailed Jun. 9, 2022", 5 pgs.
Libby, B, et al., "Validation of Monte Carlo generated phase-space descriptions of medical linear accelerators", Medical Physics, AIP, Melville, NY, US, vol. 26, No. 8, (Aug. 1, 1999), 8 pgs.
Sarrut, David, et al., "Generative Adversarial Networks (GAN) for compact beam sourcemodelling in Monte Carlo simulations", arxiv.org, Cornell University Library, 201 Olin Library Cornell University Ithaca, NY 14853, (Jul. 31, 2019), 17 pgs.
"International Application Serial No. PCT EP2021 075541, International Preliminary Report on Patentability mailed Mar. 28, 2024", 7 pgs.
"European Application Serial No. 21782454.9, Response to Communication Pursuant to Rules 161 and 162 EPC filed Oct. 22, 2024", 13 pgs.
"European Application Serial No. 21782454.9, Communication Pursuant to Article 943 EPC mailed Jan. 15, 2026", 4 pgs.

* cited by examiner

GENERATIVE MODEL OF PHASE SPACE

PRIORITY APPLICATIONS

This application is a U.S. National Stage Filing under 35 U.S.C. § 371 from International Application No. PCT/EP2021/075541, filed on Sep. 16, 2021, and published as WO2023/041167 on Mar. 23, 2023; the benefit of priority of which is hereby claimed herein, and which application and publication is hereby incorporated herein by reference in its entirety.

TECHNICAL FIELD

Embodiments of the present disclosure pertain generally to simulating dose deposition in a radiation therapy treatment system.

BACKGROUND

Radiation therapy (or "radiotherapy") can be used to treat cancers or other ailments in mammalian (e.g., human and animal) tissue. External beam radiotherapy employs a device that emits high-energy particles (e.g., photons, electrons, protons, ions and the like) to irradiate a patient. One such radiotherapy technique is a Gamma Knife, by which a patient is irradiated by a large number of low-intensity gamma rays that converge with high intensity and high precision at a target (e.g., a tumor). In another embodiment, external beam radiotherapy is provided using a linear accelerator. Another form of radiotherapy is brachytherapy, where a radiation source is placed inside or next to the area requiring treatment.

The placement, direction, and shape of the radiation field must be accurately controlled to ensure the target receives the prescribed radiation dose, and the radiation from the beam should minimize damage to the surrounding healthy tissue, often called the organ(s) at risk (OARs). Radiation dose is termed "prescribed" because a physician orders a predefined amount of radiation dose to the target and surrounding organs similar to a prescription for medicine.

The treatment planning procedure may include using a three-dimensional (3D) image of the patient to identify a target region (e.g., the tumor) and to identify critical organs near the tumor. Creation of a treatment plan can be a time-consuming process where a planner tries to comply with various treatment objectives or constraints (e.g., dose volume histogram (DVH), overlap volume histogram (OVH)), taking into account their individual importance (e.g., weighting or clinical preferences) in order to produce a treatment plan that is clinically acceptable. This task can be a time-consuming trial-and-error process that is complicated by the various OARs because as the number of OARs increases (e.g., a dozen or more for a head-and-neck treatment), so does the complexity of the process. OARs distant from a tumor may be easily spared from radiation, while OARs close to or overlapping a target tumor may be difficult to spare.

Traditionally, for each patient, the initial treatment plan can be generated in an "offline" manner. The treatment plan can be developed well before radiation therapy is delivered, such as using one or more medical imaging techniques. Imaging information can include, for example, images from X-rays, computed tomography (CT), nuclear magnetic resonance (MR), positron emission tomography (PET), single-photon emission computed tomography (SPECT), or ultrasound. A health care provider, such as a physician, may use 3D imaging information indicative of the patient anatomy to identify one or more target tumors along with the OARs near the tumor(s). The health care provider can delineate the target tumor that is to receive a prescribed radiation dose using a manual technique, and the health care provider can similarly delineate nearby tissue, such as organs, at risk of damage from the radiation treatment. Alternatively, or additionally, an automated tool (e.g., ABAS provided by Elekta AB, Sweden) can be used to assist in identifying or delineating the target tumor and organs at risk. A radiation therapy treatment plan ("treatment plan") can then be created using numerical optimization techniques that minimize objective functions composed of clinical and dosimetric objectives and constraints (e.g., the maximum, minimum, and fraction of dose of radiation to a fraction of the tumor volume ("95% of target shall receive no less than 100% of prescribed dose"), and like measures for the critical organs). The optimized plan is comprised of numerical parameters that specify, for instance, the direction, cross-sectional shape, and intensity of each radiation beam.

The treatment plan can then be later executed by positioning the patient in the treatment machine and delivering the prescribed radiation therapy directed by the optimized plan parameters. The radiation therapy treatment plan can include dose "fractioning," whereby a sequence of radiation treatments is provided over a predetermined period of time (e.g., 30-45 daily fractions), with each treatment including a specified fraction of a total prescribed dose. However, during treatment, the position of the patient and the position of the target tumor in relation to the treatment machine (e.g., linear accelerator—"linac") is very important in order to ensure the target tumor and not healthy tissue is irradiated.

Overview

In some embodiments, methods, systems and computer-readable medium are provided for simulating dose deposition in a region of interest, such as in a patient. The methods, systems and computer-readable medium perform operations comprising: receiving a set of training data representing phase space of a radiotherapy treatment device comprising propagation and scattering of particles inside the radiotherapy treatment device; training a generative machine learning model based on the set of training data to generate one or more samples of the phase space of the radiotherapy treatment device; and simulating dose deposition at a particular region of interest based on the one or more samples of the phase space generated by the generative machine learning model.

In some examples, at least one region of interest is located in a patient.

In some examples, a radiotherapy treatment plan for a patient is generated based on the simulated dose deposition.

In some examples, the set of training data describes position and momentum vectors of relevant particles within a set of regions of the radiotherapy treatment device.

In some examples, the one or more samples represent propagation and scattering of particles in a region different from the set of regions of the radiotherapy treatment device.

In some examples, the generative machine learning model comprises a neural network comprising at least one of a generative adversarial network (GAN), a variational autoencoder (VAE), a normalizing flow network, or a diffusion model.

In some examples, the set of training data represent the phase space as a collection of samples from a probability distribution.

In some examples, the operations further comprise generating the set of training data by performing a Monte Carlo simulation, wherein the set of training data is stored and retrieved from a non-volatile storage device or is computed in real time.

In some examples, the set of training data comprises multi-dimensional surface representing physical information about the particles.

In some examples, the trained generative machine learning model is stored on a same processing device that simulates the dose deposition when simulating the dose deposition.

In some examples, the operations further comprise generating a three-dimensional (3D) volume of the dose deposition based on interaction between the one or more samples and an image detector, and wherein the generative machine learning model is part of or separate from a radiotherapy system that includes the image detector.

In some examples, the generative machine learning model comprises a generative adversarial network (GAN) configured to train a generative model using a discriminative model; and values applied by the generative model and the discriminative model are established using adversarial training between the discriminative model and the generative model.

In some examples, the adversarial training comprises: training the generative model to generate a first synthetic sample of the phase space from a distribution of the particles within the phase space of the radiotherapy treatment device; and training the discriminative model to classify the first synthetic sample as a synthetic or a real training particle within the phase space of the radiotherapy treatment device; and an output of the generative model is used for training the discriminative model and an output of the discriminative model is used for training the generative model.

In some examples, the operations further comprise: obtaining a particle from the set of training data; and computing training loss for the discriminative model based on a result of comparing the classification output by the discriminative model with the particle obtained from the set of training data.

In some examples, the first synthetic sample is generated based on a random point within the phase space or a specified region within the phase space.

In some examples, the generative machine learning model comprises a normalizing flow network, and the operations further comprise: obtaining a particle from the set of training data; computing training loss based on a likelihood of the particle obtained from the set of training data based on a distribution provided by the normalizing flow network; and updating the distribution provided by the normalizing flow network based on the training loss.

In some examples, the operations further comprise computing a new particle based on a distribution provided by the normalizing flow network, wherein the new particle is computed based on a random point within the phase space or a specified region within the phase space.

In some embodiments, methods, systems and computer-readable medium are provided for simulating dose deposition in a region of interest, such as in a patient. The methods, systems and computer-readable medium perform operations comprising: accessing a generative machine learning model that has been trained based on a set of training data to generate one or more samples of phase space of a radiotherapy treatment device, the set of training data comprising propagation and scattering of particles inside the radiotherapy treatment device; and simulating dose deposition at a particular region of interest based on the one or more samples of the phase space generated by the generative machine learning model.

The above overview is intended to provide an overview of subject matter of the present patent application. It is not intended to provide an exclusive or exhaustive explanation of the inventive subject matter. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
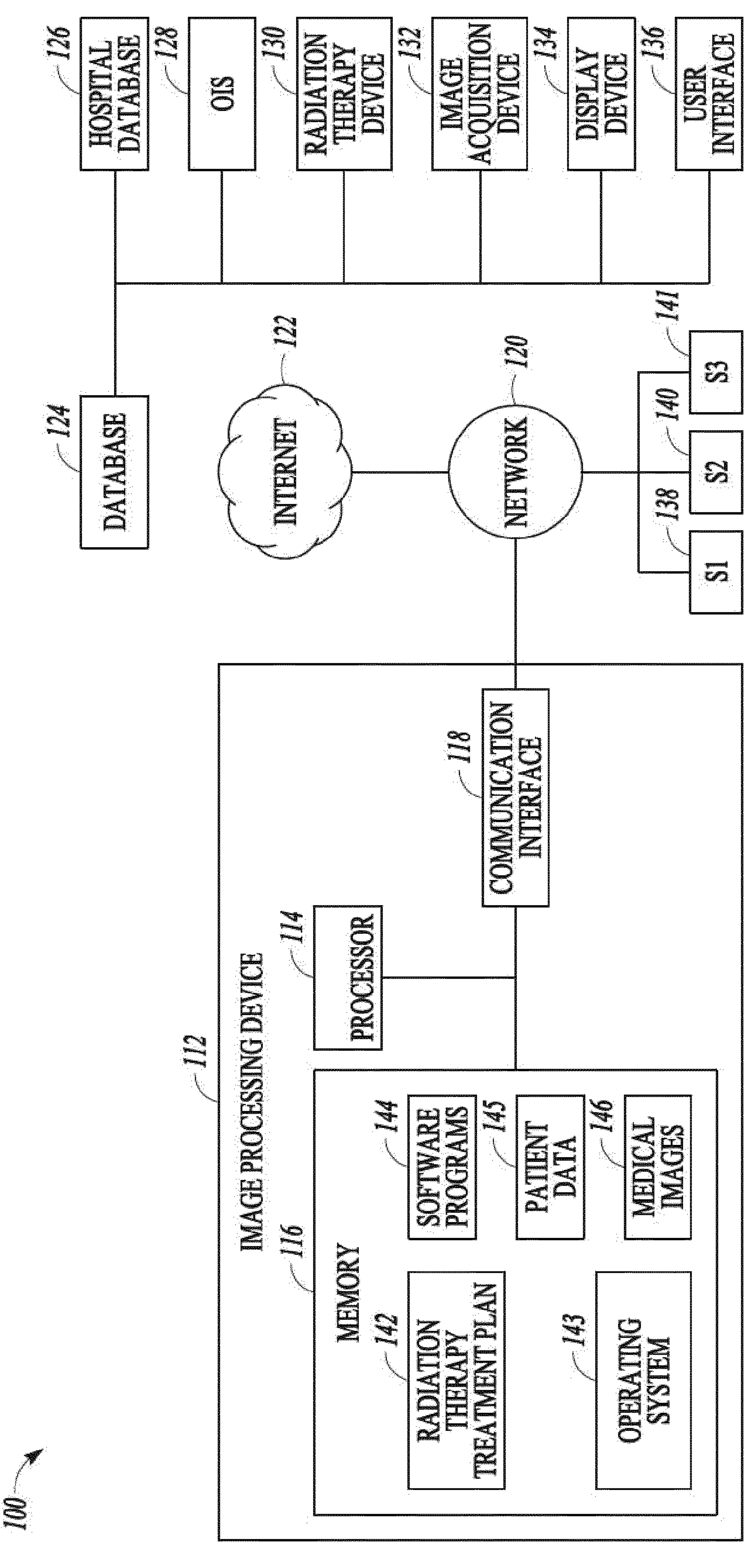
FIG. 1 illustrates an example radiotherapy system, according to some embodiments of the present disclosure.

In the following detailed description, reference is made to the accompanying drawings which form a part hereof, and which is shown by way of illustration-specific embodiments in which the present disclosure may be practiced. These embodiments, which are also referred to herein as "examples," are described in sufficient detail to enable those skilled in the art to practice the disclosure, and it is to be understood that the embodiments may be combined, or that other embodiments may be utilized and that structural, logical and electrical changes may be made without departing from the scope of the present disclosure. The following detailed description is, therefore, not to be taken in a limiting sense, and the scope of the present disclosure is defined by the appended claims and their equivalents.

Intensity modulated radiotherapy (IMRT) and volumetric modulated arc therapy (VMAT) have become the standards of care in modern cancer radiation therapy. Creating individual patient IMRT or VMAT treatment plans is a trial-and-error process, weighing target dose versus OAR sparing tradeoffs, and adjusting program constraints whose effects on the plan quality metrics and the dose distribution can be very difficult to anticipate. Indeed, the order in which the planning constraints are adjusted can itself result in dose differences. Treatment plan quality depends on often subjective judgements by the planner that depend on his/her experience and skill. Even the most skilled planners still have no assurance that their plans are close to the best possible, or whether a little or a lot of effort will result in a significantly better plan.

In the process of preparing a radiotherapy treatment plan, the amount of dose delivered to a region of interest can be considered. Monte Carlo simulation is the gold standard for dose calculation. Compared to other methods, Monte Carlo is also easier to generalize to incorporate different physical phenomena such as particle transport in the presence of electromagnetic fields. To use Monte Carlo simulations in radiotherapy treatment planning, the simulation is often performed in two phases. The first phase typically requires enormous computational resources and can run for a long time. This first phase entails the simulation of the beam generation, propagation and scattering of particles inside the radiotherapy treatment machine. The output of the first phase is typically provided as a large file that contains the phase space—a 5D or 6D surface that contains or represents all the relevant physical information about the simulated particles.

The second phase of the simulation applies the phase space computed in the first phase to a region of interest. Specifically, the second phase simulates the dose deposition (provides a dose calculation) in a particular position. The process of performing the second phase necessarily relies on the output of the first phase and the speed at which the second phase can be completed depends on the time it takes to retrieve the large file output by the first phase. Even if a parallel processor or other very fast processing device is used to generate the output of the second phase, the speed at which such a processing device can generate the output is hampered by the time it takes to read the phase space information (output of the first phase) from a non-volatile storage device, such as a hard disk.

The present disclosure includes various techniques to improve and enhance radiotherapy treatment by providing a generative machine learning model that predicts, estimates or generates samples of a phase space of a radiotherapy system to simulate dose deposition in a region of interest, such as in a patient's delineated anatomy. Namely, rather than retrieving a pre-calculated set of samples of the phase space from a non-volatile storage device, such as an output of the first phase of the Monte Carlo simulation in order to simulate dose deposition (e.g., perform the second phase of the Monte Carlo simulation), the disclosed techniques provides a generative machine learning model that predicts, estimates or generates samples of a phase space to avoid having to access such data from the non-volatile storage device (e.g., a hard drive). The technical benefits include reduced radiotherapy treatment plan creation time. The disclosed techniques may be applicable to a variety of medical treatment and diagnostic settings or radiotherapy treatment equipment and devices. In some cases, the generative machine learning model includes a neural network, such as a generative adversarial network (GAN), a variational autoencoder (VAE), a normalizing flow network, or a diffusion model.

According to some embodiments, the disclosure, in-directly or directly, learns (trains a generative machine learning model based on) the phase space of a radiotherapy treatment device comprising propagation and scattering of particles inside the radiotherapy treatment device. For example, a Monte Carlo simulation is calculated (e.g., first phase of the Monte Carlo simulation is performed) to generate a phase space of the radiotherapy treatment device (e.g., provide data that describes position and momentum vectors of relevant particles within a set of regions of the radiotherapy treatment device). Then, the generative machine learning model is trained based on the output of the first phase of the Monte Carlo simulation. After training the generative machine learning model, the machine learning model can be stored and executed by a same processing device that is used to calculate or simulate dose deposition in a region of interest. Namely, the processing device can use the generative machine learning model to generate one or more samples of the phase space (without having to re-calculate or obtain precalculated samples using a Monte Carlo simulation) and can then use the output of the model to simulate dose deposition in a patient. In some cases, the one or more samples generated by the generative model represent propagation and scattering of particles in a region different from a set of regions of the radiotherapy treatment device calculated by the Monte Carlo simulation. The simulated dose deposition can then be used to generate a radiotherapy treatment plan for the patient.

In this way, by using machine learning to generate the samples of the phase space of a radiotherapy device, computational complexity of the total plan optimization process is reduced, and the time needed to create a treatment plan for a given patient is reduced.

FIG. 1 illustrates an example radiotherapy system 100 for providing radiation therapy to a patient. The radiotherapy system 100 includes an image processing device 112 (e.g., a data processing device). The image processing device 112 may be connected to a network 120. The network 120 may be connected to the Internet 122. The network 120 can connect the image processing device 112 with one or more of a database 124, a hospital database 126, an oncology information system (OIS) 128, a radiation therapy device 130, an image acquisition device 132, a display device 134, and a user interface 136. The image processing device 112 can be configured to generate radiation therapy treatment plans 142 to be used by the radiation therapy device 130. In some implementations, some or all of the components of the image processing device 112 can be integrated or incorporated into any one of the database 124, a hospital database 126, an oncology information system (OIS) 128, a radiation therapy device 130, an image acquisition device 132, a display device 134, and/or a user interface 136.

As an example, the image processing device 112 can include a processor 114 that stores in a memory 116 a trained generative machine learning model for generating or predicting samples of a phase space of the radiation therapy device 130. In an example, the image processing device 112 can also locally store parameters of a target region of interest and can simulate dose deposition in the target region based on the predicted samples and the parameters of the target region. In another example, the radiation therapy device 130 (e.g., a Linac or MR-Linac) can include a local processor (not shown) that stores another instance of the trained generative machine learning model for generating or predicting samples of a phase space of the radiation therapy device 130. The processor of the radiation therapy device 130 can also locally store or retrieve parameters of a target region of interest (e.g., from the database 124 or the memory device 116) and can simulate dose deposition in the target region based on the predicted samples and the parameters of the target region.

The image processing device 112 may include a memory device 116, an processor 114, and a communication interface 118. The memory device 116 may store computer-executable instructions, such as an operating system 143, radiation therapy treatment plans 142 (e.g., original treatment plans, adapted treatment plans and the like), software programs 144 (e.g., artificial intelligence, deep learning, neural networks, radiotherapy treatment plan software, trained generative machine learning model(s) for generating samples of a phase space of one or more radiation therapy devices 130), and any other computer-executable instructions to be executed by the processor 114.

In one embodiment, the software programs 144 may convert medical images of one format (e.g., MRI) to another format (e.g., CT) by producing synthetic images, such as pseudo-CT images. For instance, the software programs 144 may include image processing programs to train a predictive model for converting a medical image 146 in one modality (e.g., an MRI image) into a synthetic image of a different modality (e.g., a pseudo CT image); alternatively, the trained predictive model may convert a CT image into an MRI image. In another embodiment, the software programs 144 may register the patient image (e.g., a CT image or an MR image) with that patient's dose distribution (also represented as an image) so that corresponding image voxels and dose voxels are associated appropriately by the network. In yet another embodiment, the software programs 144 may substitute functions of the patient images such as signed distance functions or processed versions of the images that emphasize some aspect of the image information. Such functions might emphasize edges or differences in voxel textures or any other structural aspect useful to neural network learning. In another embodiment, the software programs 144 may substitute functions of the dose distribution that emphasize some aspect of the dose information. Such functions might emphasize steep gradients around the target or any other structural aspect useful to neural network learning. The memory device 116 may store data, including medical images 146, patient data 145, and other data required to create and implement a radiation therapy treatment plan 142.

In yet another embodiment, the software programs 144 may use a generative machine learning model (e.g., a generative adversarial network (GAN), a variational autoencoder (VAE), a normalizing flow network, and/or a diffusion model) generate one or more samples of the phase space of the radiation therapy devices 130 and can simulate dose deposition at a particular region of interest based on the one or more samples of the phase space generated by the generative machine learning model. For example, the software programs 144 can store or access the generative machine learning model which has been previously trained to generate samples of the phase space and can generate samples of the phase space based on an output of the generative machine learning model. The software programs 144 obtain one or more parameters associated with the region of interest (e.g., by accessing one or more images of a patient). The software programs 144 can then perform the second phase of the Monte Carlo simulation based on the generated samples and the one or more parameters associated with the region of interest to simulate the dose deposition in the region of interest. The software programs 144 can use the simulated dose deposition to generate a radiotherapy treatment plan for the patient.

In one example, the software programs 144 train the generative machine learning model based on training data representing phase space of the radiation therapy device 130. The training data can be stored locally on image processing device 112 or retrieved via network 120 from database 124, hospital database 126, OIS 128, radiation therapy device 130 and/or image acquisition device 132. The phase space of the radiation therapy devices 130 in the trained data includes propagation and scattering of particles inside the radiation therapy device 130. In an example, the software programs 144 generate the training data by performing a first phase (e.g., a long run) of a Monte Carlo simulation on the parameters of the radiation therapy device 130. The output of the Monte Carlo simulation provides a collection of samples from a probability distribution and/or describes position and momentum vectors of relevant particles within a set of regions of the radiation therapy device 130 (e.g., the radiotherapy treatment device). The collection of samples generated by the output of the first phase of the Monte Carlo simulation is stored in the memory device 116. The generative machine learning model can be trained in a supervised or unsupervised manner. In one implementation, the sample generated by the generative machine learning model represents propagation and scattering of particles in a region different from the set of regions of the radiotherapy treatment device described by the training data. Namely, the Monte Carlo simulation can be used to provide training data for a particular set of regions of the radiotherapy treatment device and after the generative machine learning mode is trained based on such training data, the generative machine learning model can generate predictions of samples for other regions of the radiotherapy treatment device not covered by the samples in the training data. The software programs 144 perform a plurality of iterations of the training operations across additional batches of the training data until a stopping criterion is met.

In one example, the generative machine learning model is a GAN in which a generative model is trained using a discriminative model. In such circumstances, values applied by the generative model and the discriminative model are established using adversarial training between the discriminative model and the generative model. For examples, the adversarial training includes training the generative model to generate a first synthetic sample of the phase space (e.g., based on a random point within the phase space or a specified region within the phase space) from a distribution of the particles within the phase space of the radiotherapy treatment device. The discriminative model is trained to classify the first synthetic sample as a synthetic or a real training particle within the phase space of the radiotherapy treatment device. An output of the generative model is used for training the discriminative model and an output of the discriminative model is used for training the generative model. Specifically, parameters of the generative model and the discriminative model are updated based on the classification of the discriminative model with respect to the underlying training data. In one implementation, a particle is obtained from the set of training data and training loss for the discriminative model is computed based on a result of comparing the classification output by the discriminative model with the particle obtained from the set of training data.

In another example, the generative machine learning model includes a normalizing flow network. In such cases, a new particle (e.g., based on a random point within the phase space or a specified region within the phase space) is computed based on a distribution provided by the normalizing flow network. The training loss is computed based on a likelihood of a particle obtained from the set of training data. The distribution provided by the normalizing flow network is updated based on the training loss.

In addition to the memory device 116 storing the software programs 144, it is contemplated that software programs 144 may be stored on a removable computer medium, such as a hard drive, a computer disk, a CD-ROM, a DVD, a HD, a Blu-Ray DVD, USB flash drive, a SD card, a memory stick, or any other suitable medium; and when downloaded to image processing device 112, the software programs 144 may be executed by processor 114.

The processor 114 may be communicatively coupled to the memory device 116, and the processor 114 may be configured to execute computer-executable instructions stored thereon. The processor 114 may send or receive medical images 146 to memory device 116. For example, the processor 114 may receive medical images 146 from the image acquisition device 132 via the communication interface 118 and network 120 to be stored in memory device 116. The processor 114 may also send medical images 146 stored in memory device 116 via the communication interface 118 to the network 120 to be either stored in database 124 or the hospital database 126.

Further, the processor 114 may utilize software programs 144 (e.g., a treatment planning software) along with the medical images 146 and patient data 145 to create the radiation therapy treatment plan 142. Medical images 146 may include information such as imaging data associated with a patient anatomical region, organ, or volume of interest segmentation data. Patient data 145 may include information such as (1) functional organ modeling data (e.g., serial versus parallel organs, appropriate dose response models, etc.); (2) radiation dosage data (e.g., DVH information; or (3) other clinical information about the patient and course of treatment (e.g., other surgeries, chemotherapy, previous radiotherapy, etc.).

In addition, the processor 114 may utilize software programs to generate intermediate data such as updated parameters to be used, for example, by a machine learning model, such as a neural network model; or generate intermediate 2D or 3D images, which may then subsequently be stored in memory device 116. The processor 114 may subsequently then transmit the executable radiation therapy treatment plan 142 via the communication interface 118 to the network 120 to the radiation therapy device 130, where the radiation therapy plan will be used to treat a patient with radiation. In addition, the processor 114 may execute software programs 144 to implement functions such as image conversion, image segmentation, artefact correction, dimensionality reduction and function estimation. For instance, the processor 114 may execute software programs 144 that train or contour a medical image; such software programs 144 when executed may train a boundary detector or utilize a shape dictionary.

The processor 114 may be a processing device, include one or more general-purpose processing devices such as a microprocessor, a central processing unit (CPU), a graphics processing unit (GPU), an accelerated processing unit (APU), or the like. More particularly, the processor 114 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 114 may also be implemented by one or more special-purpose processing devices such as an application-specific integrated circuit (ASIC), a field programmable gate array (FPGA), a digital signal processor (DSP), a System on a Chip (SoC), or the like. As would be appreciated by those skilled in the art, in some embodiments, the processor 114 may be a special-purpose processor, rather than a general-purpose processor. The processor 114 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processor 114 may also include graphical processing units such as a GPU from the GeForce®, Quadro®, Tesla® family manufactured by Nvidia™, GMA, Iris™ family manufactured by Intel™, or the Radeon™ family manufactured by AMD™. The processor 114 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor (for example, a multi-core design or a plurality of processors each having a multi-core design). The processor 114 can execute sequences of computer program instructions, stored in memory device 116, to perform various operations, processes, methods that will be explained in greater detail below.

The memory device 116 can store medical images 146. In some embodiments, the medical images 146 may include one or more MRI images (e.g., two-dimensional (2D) MRI, 3D MRI, 2D streaming MRI, four-dimensional (4D) MRI, 4D volumetric MRI, 4D cine MRI, projection images, graphical aperture images, and pairing information between projection images and graphical aperture images, etc.), functional MRI images (e.g., fMRI, DCE-MRI, diffusion MRI), CT images (e.g., 2D CT, cone beam CT, 3D CT, 4D CT), ultrasound images (e.g., 2D ultrasound, 3D ultrasound, 4D ultrasound), one or more projection images representing views of an anatomy depicted in the MRI, synthetic CT (pseudo-CT), and/or CT images at different angles of a gantry relative to a patient axis, PET images, X-ray images, fluoroscopic images, radiotherapy portal images, SPECT images, computer generated synthetic images (e.g., pseudo-CT images), training data representing a phase space provided by a long run Monte Carlo simulation, and the like. Further, the medical images 146 may also include medical image data, for instance, training images, and training images, contoured images, and dose images. In an embodiment, the medical images 146 may be received from the image acquisition device 132. Accordingly, image acquisition device 132 may include an MRI imaging device, a CT imaging device, a PET imaging device, an ultrasound imaging device, a fluoroscopic device, a SPECT imaging device, an integrated linac and MRI imaging device, or other medical imaging devices for obtaining the medical images of the patient. The medical images 146 may be received and stored in any type of data or any type of format that the image processing device 112 may use to perform operations consistent with the disclosed embodiments.

The memory device 116 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a CD-ROM, a DVD or other optical storage, a cassette tape, other magnetic storage device, or any other non-transitory medium that may be used to store information including image, data, or computer executable instructions (e.g., stored in any format) capable of being accessed by the processor 114, or any other type of computer device. The computer program instructions can be accessed by the processor 114, read from the ROM, or any other suitable memory location, and loaded into the RAM for execution by the processor 114. For example, the memory device 116 may store one or more software applications. Software applications stored in the memory device 116 may include, for example, an operating system 143 for common computer systems as well as for software-controlled devices. Further, the memory device 116 may store an entire software application, or only a part of a software application, that are executable by the processor 114. For example, the memory device 116 may store one or more radiation therapy treatment plans 142.

The image processing device 112 can communicate with the network 120 via the communication interface 118, which can be communicatively coupled to the processor 114 and the memory device 116. The communication interface 118 may provide communication connections between the image processing device 112 and radiotherapy system 100 components (e.g., permitting the exchange of data with external devices). For instance, the communication interface 118 may in some embodiments have appropriate interfacing circuitry to connect to the user interface 136, which may be a hardware keyboard, a keypad, or a touch screen through which a user may input information into radiotherapy system 100.

Communication interface 118 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE, 5G and the like), and the like. Communication interface 118 may include one or more digital and/or analog communication devices that permit image processing device 112 to communicate with other machines and devices, such as remotely located components, via the network 120.

The network 120 may provide the functionality of a local area network (LAN), a wireless network, a cloud computing environment (e.g., software as a service, platform as a service, infrastructure as a service, etc.), a client-server, a wide area network (WAN), and the like. For example, network 120 may be a LAN or a WAN that may include other systems S1 (138), S2 (140), and S3 (141). Systems S1, S2, and S3 may be identical to image processing device 112 or may be different systems. In some embodiments, one or more of the systems in network 120 may form a distributed computing/simulation environment that collaboratively performs the embodiments described herein. In some embodiments, one or more systems S1, S2, and S3 may include an image acquisition device 132. In addition, network 120 may be connected to Internet 122 to communicate with servers and clients that reside remotely on the Internet.

Therefore, network 120 can allow data transmission between the image processing device 112 and a number of various other systems and devices, such as the OIS 128, the radiation therapy device 130, and the image acquisition device 132. Further, data generated by the OIS 128 and/or the image acquisition device 132 may be stored in the memory device 116, the database 124, and/or the hospital database 126. The data may be transmitted/received via network 120, through communication interface 118 in order to be accessed by the processor 114, as required.

The image processing device 112 may communicate with database 124 through network 120 to send/receive a plurality of various types of data stored on database 124. For example, database 124 may include machine data (control points or radiotherapy treatment device parameters) that includes information associated with a radiation therapy device 130, image acquisition device 132, or other machines relevant to radiotherapy. Machine data information may include control points, such as radiation beam size, arc placement, beam on and off time duration, machine parameters, segments, MLC configuration, gantry speed, MRI pulse sequence, and the like. Database 124 may be a storage device and may be equipped with appropriate database administration software programs. One skilled in the art would appreciate that database 124 may include a plurality of devices located either in a central or a distributed manner.

In some embodiments, database 124 may include a processor-readable storage medium (not shown). While the processor-readable storage medium in an embodiment may be a single medium, the term "processor-readable storage medium" should be taken to include a single medium or multiple media (e.g., a centralized or distributed database, and/or associated caches and servers) that store the one or more sets of computer-executable instructions or data. The term "processor-readable storage medium" shall also be taken to include any medium that is capable of storing or encoding a set of instructions for execution by a processor and that cause the processor to perform any one or more of the methodologies of the present disclosure. The term "processor-readable storage medium" shall accordingly be taken to include, but not be limited to, solid-state memories, optical and magnetic media. For example, the processor-readable storage medium can be one or more volatile, non-transitory, or non-volatile tangible computer-readable media.

Processor 114 may communicate with database 124 to read images into memory device 116 or store images from memory device 116 to database 124. For example, the database 124 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DIMCOM) data, projection images, graphical aperture images, etc.) that the database 124 received from image acquisition device 132. Database 124 may store data to be used by the processor 114 when executing software program 144, or when creating radiation therapy treatment plans 142. Database 124 may store the data produced by the trained machine leaning mode, such as a neural network including the network parameters constituting the model learned by the network and the resulting predicted data. The image processing device 112 may receive the imaging data, such as a medical image 146 (e.g., 2D MRI slice images, CT images, 2D Fluoroscopy images, X-ray images, 3D MRI images, 4D MRI images, projection images, graphical aperture images, etc.) either from the database 124, the radiation therapy device 130 (e.g., an MRI-linac), and/or the image acquisition device 132 to generate a treatment plan 142.

In an embodiment, the radiotherapy system 100 can include an image acquisition device 132 that can acquire medical images (e.g., MRI images, 3D MRI, 2D streaming MRI, 4D volumetric MRI, CT images, cone-Beam CT, PET images, functional MRI images (e.g., fMRI, DCE-MRI and diffusion MRI), X-ray images, fluoroscopic image, ultrasound images, radiotherapy portal images, SPECT images, and the like) of the patient. Image acquisition device 132 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the image acquisition device 132 can be stored within database 124 as either imaging data and/or test data. By way of example, the images acquired by the image acquisition device 132 can also be stored by the image processing device 112, as medical images 146 in memory device 116.

In an embodiment, for example, the image acquisition device 132 may be integrated with the radiation therapy device 130 as a single apparatus (e.g., an MRI-linac). Such an MRI-linac can be used, for example, to determine a location of a target organ or a target tumor in the patient, so as to direct radiation therapy accurately according to the radiation therapy treatment plan 142 to a predetermined target.

The image acquisition device 132 can be configured to acquire one or more images of the patient's anatomy for a region of interest (e.g., a target organ, a target tumor, or both). Each image, typically a 2D image or slice, can include one or more parameters (e.g., a 2D slice thickness, an orientation, and a location, etc.). In an embodiment, the image acquisition device 132 can acquire a 2D slice in any orientation. For example, an orientation of the 2D slice can include a sagittal orientation, a coronal orientation, or an axial orientation. The processor 114 can adjust one or more parameters, such as the thickness and/or orientation of the 2D slice, to include the target organ and/or target tumor. In an embodiment, 2D slices can be determined from information such as a 3D MRI volume. Such 2D slices can be acquired by the image acquisition device 132 in "real-time" while a patient is undergoing radiation therapy treatment, for example, when using the radiation therapy device 130, with "real-time" meaning acquiring the data in at least milliseconds or less.

The image processing device 112 may generate and store radiation therapy treatment plans 142 for one or more patients. The radiation therapy treatment plans 142 may provide information about a particular radiation dose to be applied to each patient. The radiation therapy treatment plans 142 may also include other radiotherapy information, such as control points including beam angles, gantry angles, beam intensity, dose-histogram-volume information, the number of radiation beams to be used during therapy, the dose per beam, and the like.

The processor 114 may generate the radiation therapy treatment plan 142 by using software programs 144 such as treatment planning software (such as Monaco®, manufactured by Elekta AB of Stockholm, Sweden). In order to generate the radiation therapy treatment plans 142, the processor 114 may communicate with the image acquisition device 132 (e.g., a CT device, an MRI device, a PET device, an X-ray device, an ultrasound device, etc.) to access images of the patient and to delineate a target, such as a tumor. In some embodiments, the delineation of one or more OARs, such as healthy tissue surrounding the tumor or in close proximity to the tumor, may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the radiotherapy system 100 may study the dose distribution not only in the target but also in the OAR.

In order to delineate a target organ or a target tumor from the OAR, medical images, such as MRI images, CT images, PET images, fMRI images, X-ray images, ultrasound images, radiotherapy portal images, SPECT images, and the like, of the patient undergoing radiotherapy may be obtained non-invasively by the image acquisition device 132 to reveal the internal structure of a body part. Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as MONACO™ manufactured by Elekta AB of Stockholm, Sweden) or automatically (e.g., using a program such as the Atlas-based auto-segmentation software, ABAS™, and a successor auto-segmentation software product ADMIRE™, manufactured by Elekta AB of Stockholm, Sweden). In certain embodiments, the 3D structure of a target tumor or an OAR may be generated automatically by the treatment planning software.

After the target tumor and the OAR(s) have been located and delineated, a dosimetrist, physician, or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), such as using the generative machine learning model that predicts a sample from the phase space, a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive≤45Gy, ≤55Gy and <54Gy, respectively). The result of inverse planning may constitute a radiation therapy treatment plan 142 that may be stored in memory device 116 or database 124. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing device 112 can generate a tailored radiation therapy treatment plan 142 having these parameters in order for the radiation therapy device 130 to provide radiotherapy treatment to the patient.

In addition, the radiotherapy system 100 may include a display device 134 and a user interface 136. The display device 134 may include one or more display screens that display medical images, interface information, treatment planning parameters (e.g., projection images, graphical aperture images, contours, dosages, beam angles, etc.), treatment plans, a target, localizing a target and/or tracking a target, or any related information to the user. The user interface 136 may be a keyboard, a keypad, a touch screen, or any type of device with which a user may input information to radiotherapy system 100. Alternatively, the display device 134 and the user interface 136 may be integrated into a device such as a tablet computer (e.g., Apple iPad®, Lenovo Thinkpad®, Samsung Galaxy®, etc.).

Furthermore, any and all components of the radiotherapy system 100 may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the image processing device 112, the OIS 128, and the image acquisition device 132 could be implemented as a virtual machine. Given the processing power, memory, and computational capability available, the entire radiotherapy system 100 could be implemented as a virtual machine.

Figure 2A:
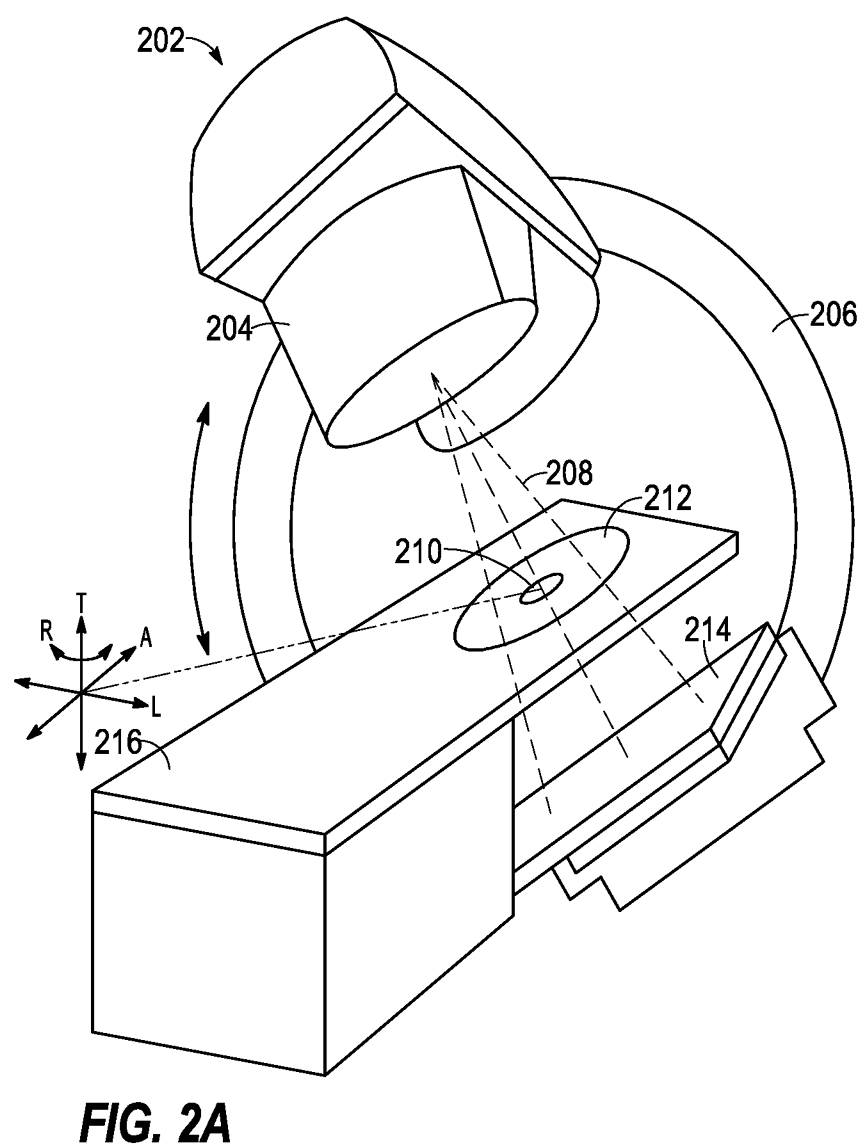
FIG. 2A illustrates an example radiation therapy system that can include radiation therapy output configured to provide a therapy beam, according to some embodiments of the present disclosure.

FIG. 2A illustrates an example radiation therapy device 202 that may include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as an MLC as described in the illustrative embodiment of FIG. 5, below.

Referring back to FIG. 2A, a patient can be positioned in a region 212 and supported by the treatment couch 216 to receive a radiation therapy dose, according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an embodiment, gantry 206 may be continuously rotatable around couch 216 when the couch 216 is inserted into the treatment area. In another embodiment, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation beam 208 according to a radiation therapy treatment plan. Both the couch 216 and the gantry 206 are independently moveable from one another in multiple degrees of freedom, which allows the patient to be positioned such that the radiation beam 208 can target the tumor precisely. The MLC may be integrated and included within gantry 206 to deliver the radiation beam 208 of a certain shape.

The coordinate system (including axes A, T, and L) shown in FIG. 2A can have an origin located at an isocenter 210. The isocenter can be defined as a location where the central axis of the radiation beam 208 intersects the origin of a coordinate axis, such as to deliver a prescribed radiation dose to a location on or within a patient. Alternatively, the isocenter 210 can be defined as a location where the central axis of the radiation beam 208 intersects the patient for various rotational positions of the radiation therapy output 204 as positioned by the gantry 206 around the axis A. As discussed herein, the gantry angle corresponds to the position of gantry 206 relative to axis A, although any other axis or combination of axes can be referenced and used to determine the gantry angle.

Gantry 206 may also have an attached imaging detector 214. The imaging detector 214 is preferably located opposite to the radiation source, and in an embodiment, the imaging detector 214 can be located within a field of the radiation beam 208.

The imaging detector 214 can be mounted on the gantry 206 (preferably opposite the radiation therapy output 204), such as to maintain alignment with the radiation beam 208. The imaging detector 214 rotates about the rotational axis as the gantry 206 rotates. In an embodiment, the imaging detector 214 can be a flat panel detector (e.g., a direct detector or a scintillator detector). In this manner, the imaging detector 214 can be used to monitor the radiation beam 208 or the imaging detector 214 can be used for imaging the patient's anatomy, such as portal imaging. The control circuitry of the radiation therapy device 202 may be integrated within the system 100 or remote from it.

In an illustrative embodiment, one or more of the couch 216, the therapy output 204, or the gantry 206 can be automatically positioned, and the therapy output 204 can establish the radiation beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue near the therapy locus can be reduced or avoided.

Figure 2B:
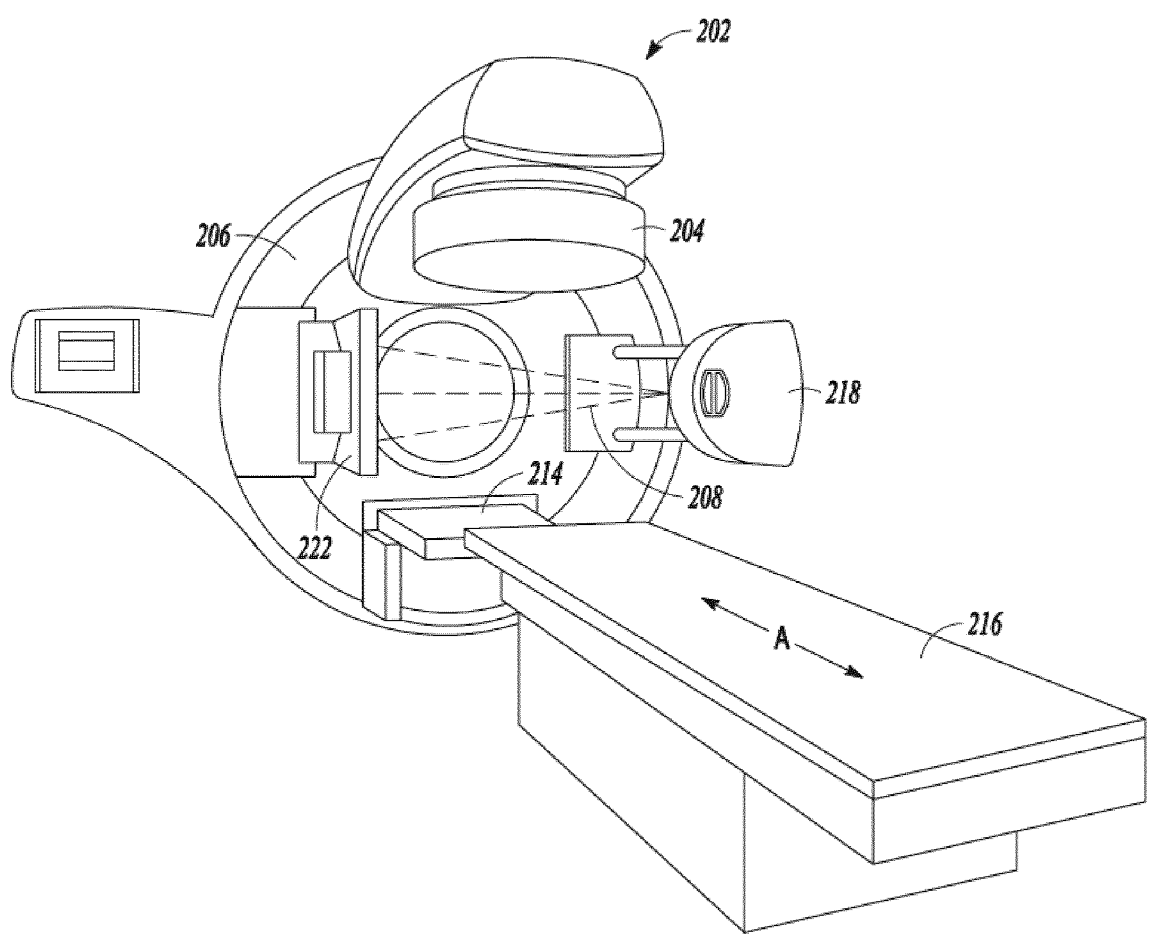
FIG. 2B illustrates an example system including a combined radiation therapy system and an imaging system, such as a cone beam computed tomography (CBCT) imaging system, according to some embodiments of the present disclosure.

FIG. 2B illustrates an example radiation therapy device 202 that may include a combined linac and an imaging system, such as a CT imaging system. The radiation therapy device 202 can include an MLC (not shown). The CT imaging system can include an imaging X-ray source 218, such as providing X-ray energy in a kiloelectron-Volt (keV) energy range. The imaging X-ray source 218 can provide a fan-shaped and/or a conical radiation beam 208 directed to an imaging detector 222, such as a flat panel detector. The radiation therapy device 202 can be similar to the system described in relation to FIG. 2A, such as including a radiation therapy output 204, a gantry 206, a couch 216, and another imaging detector 214 (such as a flat panel detector). The X-ray source 218 can provide a comparatively-lower-energy X-ray diagnostic beam for imaging.

In the illustrative embodiment of FIG. 2B, the radiation therapy output 204 and the X-ray source 218 can be mounted on the same rotating gantry 206, rotationally separated from each other by 90 degrees. In another embodiment, two or more X-ray sources can be mounted along the circumference of the gantry 206, such as each having its own detector arrangement to provide multiple angles of diagnostic imaging concurrently. Similarly, multiple radiation therapy outputs 204 can be provided.

Figure 3:
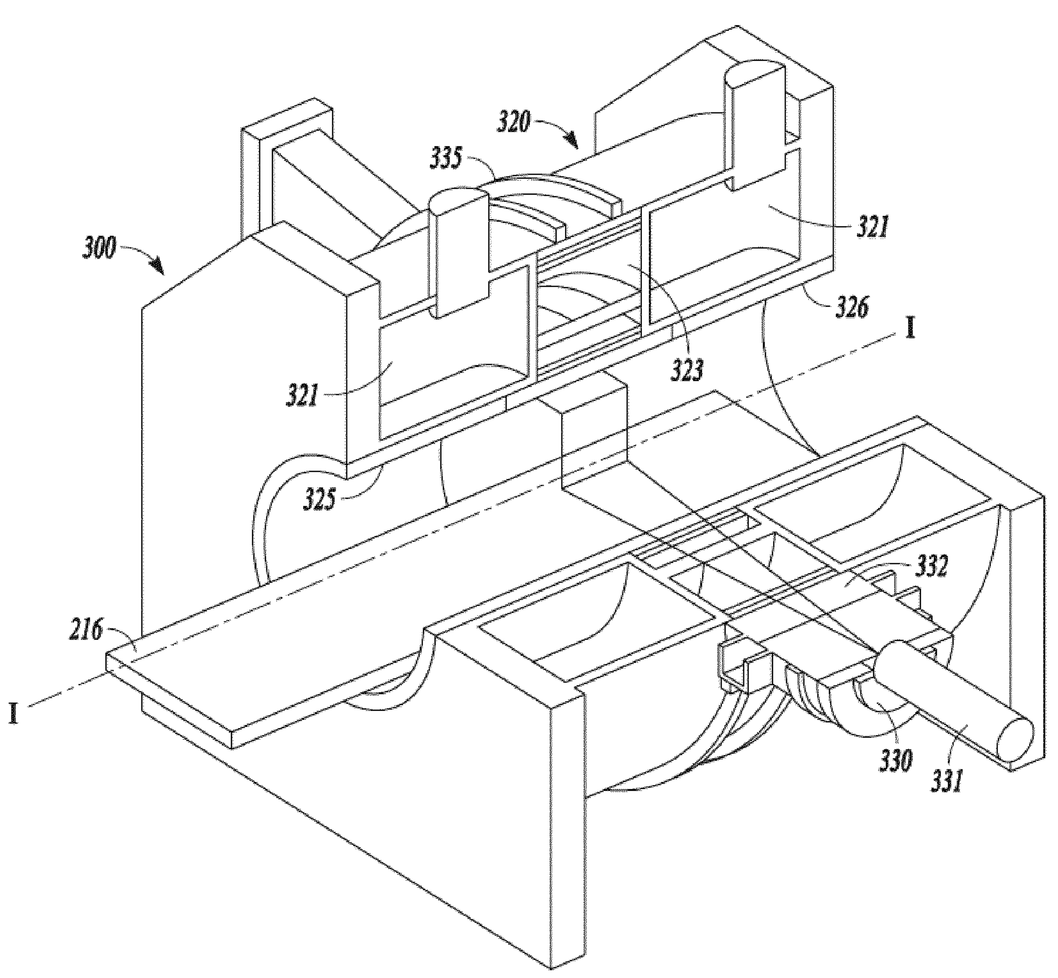
FIG. 3 illustrates a partially cut-away view of an example system including a combined radiation therapy system and an imaging system, such as a nuclear magnetic resonance (MR) imaging (MRI) system, according to some embodiments of the present disclosure.
Figure 4A:
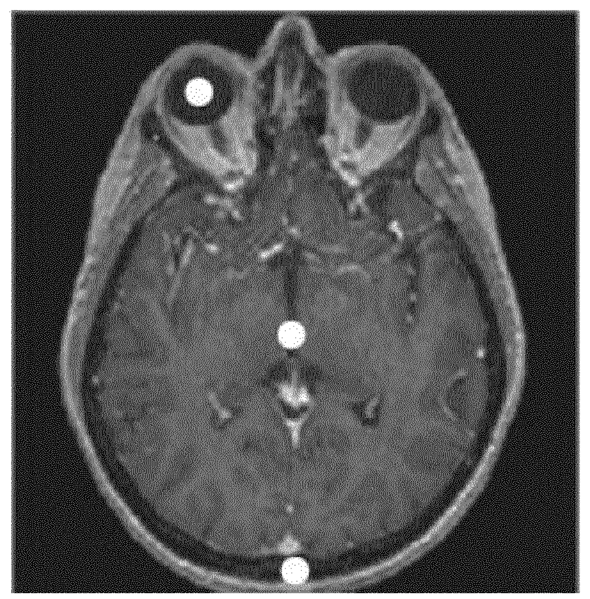
FIGS. 4A and 4B depict the differences between an example MRI image and a corresponding CT image, respectively, according to some embodiments of the present disclosure.
Figure 4B:

FIG. 3 depicts an example radiation therapy system 300 that can include combining a radiation therapy device 202 and an imaging system, such as a MR imaging system (e.g., known in the art as an MR-linac) consistent with the disclosed embodiments. As shown, system 300 may include a couch 216, an image acquisition device 320, and a radiation delivery device 330. System 300 delivers radiation therapy to a patient in accordance with a radiotherapy treatment plan. In some embodiments, image acquisition device 320 may correspond to image acquisition device 132 in FIG. 1 that may acquire origin images of a first modality (e.g., MRI image shown in FIG. 4A) or destination images of a second modality (e.g., CT image shown in FIG. 4B).

Couch 216 may support a patient (not shown) during a treatment session. In some implementations, couch 216 may move along a horizontal translation axis (labelled "I"), such that couch 216 can move the patient resting on couch 216 into and/or out of system 300. Couch 216 may also rotate around a central vertical axis of rotation, transverse to the translation axis. To allow such movement or rotation, couch 216 may have motors (not shown) enabling the couch 216 to move in various directions and to rotate along various axes. A controller (not shown) may control these movements or rotations in order to properly position the patient according to a treatment plan.

In some embodiments, image acquisition device 320 may include an MRI machine used to acquire 2D or 3D MRI images of the patient before, during, and/or after a treatment session. Image acquisition device 320 may include a magnet 321 for generating a primary magnetic field for magnetic resonance imaging. The magnetic field lines generated by operation of magnet 321 may run substantially parallel to the central translation axis I. Magnet 321 may include one or more coils with an axis that runs parallel to the translation axis I. In some embodiments, the one or more coils in magnet 321 may be spaced such that a central window 323 of magnet 321 is free of coils. In other embodiments, the coils in magnet 321 may be thin enough or of a reduced density such that they are substantially transparent to radiation of the wavelength generated by radiation delivery device 330. Image acquisition device 320 may also include one or more shielding coils, which may generate a magnetic field outside magnet 321 of approximately equal magnitude and opposite polarity in order to cancel or reduce any magnetic field outside of magnet 321. As described below, radiation source 331 of radiation delivery device 330 may be positioned in the region where the magnetic field is cancelled, at least to a first order, or reduced.

Image acquisition device 320 may also include two gradient coils 325 and 326, which may generate a gradient magnetic field that is superposed on the primary magnetic field. Coils 325 and 326 may generate a gradient in the resultant magnetic field that allows spatial encoding of the protons so that their position can be determined. Gradient coils 325 and 326 may be positioned around a common central axis with the magnet 321 and may be displaced along that central axis. The displacement may create a gap, or window, between coils 325 and 326. In embodiments where magnet 321 can also include a central window 323 between coils, the two windows may be aligned with each other.

In some embodiments, image acquisition device 320 may be an imaging device other than an MRI, such as an X-ray, a CT, a CBCT, a spiral CT, a PET, a SPECT, an optical tomography, a fluorescence imaging, ultrasound imaging, radiotherapy portal imaging device, or the like. As would be recognized by one of ordinary skill in the art, the above description of image acquisition device 320 concerns certain embodiments and is not intended to be limiting.

Figure 5:
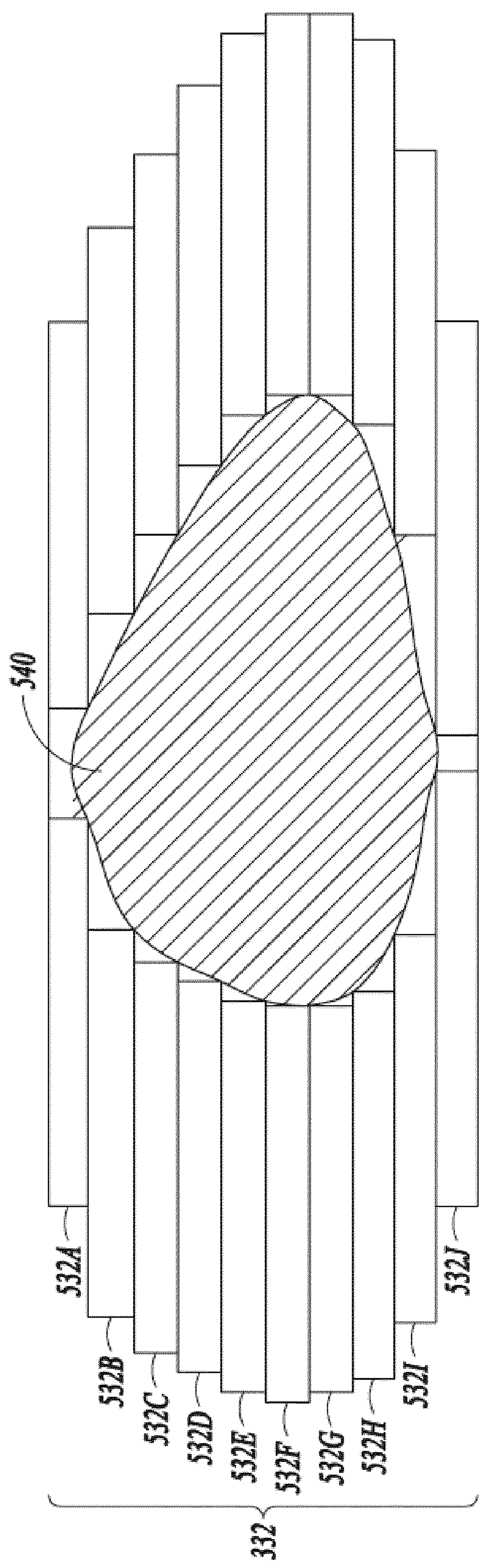
FIG. 5 illustrates an example collimator configuration for shaping, directing, or modulating an intensity of a radiation therapy beam, according to some embodiments of the present disclosure.

Radiation delivery device 330 may include the radiation source 331, such as an X-ray source or a linac, and an MLC 332 (shown below in more detail in FIG. 5). Radiation delivery device 330 may be mounted on a chassis 335. One or more chassis motors (not shown) may rotate the chassis 335 around the couch 216 when the couch 216 is inserted into the treatment area. In an embodiment, the chassis 335 may be continuously rotatable around the couch 216, when the couch 216 is inserted into the treatment area. Chassis 335 may also have an attached radiation detector (not shown), preferably located opposite to radiation source 331 and with the rotational axis of the chassis 335 positioned between the radiation source 331 and the detector. Further, the device 330 may include control circuitry (not shown) used to control, for example, one or more of the couch 216, image acquisition device 320, and radiation delivery device 330. The control circuitry of the radiation delivery device 330 may be integrated within the system 300 or remote from it.

During a radiotherapy treatment session, a patient may be positioned on couch 216. System 300 may then move couch 216 into the treatment area defined by the magnet 321, coils 325, 326, and chassis 335. Control circuitry may then control radiation source 331, MLC 332, and the chassis motor(s) to deliver radiation to the patient through the window between coils 325 and 326 according to a radiotherapy treatment plan.

FIG. 2A, FIG. 2B, and FIG. 3 illustrate generally embodiments of a radiation therapy device configured to provide radiotherapy treatment to a patient, including a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another embodiment, the therapy output can be fixed, such as located in a region laterally separated from the patient, and a platform supporting the patient can be used to align a radiation therapy isocenter with a specified target locus within the patient.

As discussed above, radiation therapy devices described by FIG. 2A, FIG. 2B, and FIG. 3 include an MLC for shaping, directing, or modulating an intensity of a radiation therapy beam to the specified target locus within the patient. FIG. 5 illustrates an example MLC 332 that includes leaves 532A through 532J that can be automatically positioned to define an aperture approximating a tumor 540 cross-section or projection. The leaves 532A through 532J permit modulation of the radiation therapy beam. The leaves 532A through 532J can be made of a material specified to attenuate or block the radiation beam in regions other than the aperture, in accordance with the radiation treatment plan. For example, the leaves 532A through 532J can include metallic plates, such as comprising tungsten, with a long axis of the plates oriented parallel to a beam direction and having ends oriented orthogonally to the beam direction (as shown in the plane of the illustration of FIG. 2A). A "state" of the MLC 332 can be adjusted adaptively during a course of radiation therapy treatment, such as to establish a therapy beam that better approximates a shape or location of the tumor 540 or another target locus. This is in comparison to using a static collimator configuration or as compared to using an MLC 332 configuration determined exclusively using an "offline" therapy planning technique. A radiation therapy technique using the MLC 332 to produce a specified radiation dose distribution to a tumor or to specific areas within a tumor can be referred to as IMRT. The resulting beam shape that is output using the MLC 332 is represented as a graphical aperture image. Namely, a given graphical aperture image is generated to represent how a beam looks (beam shape) and its intensity after being passed through and output by MLC 332.

Figure 6:
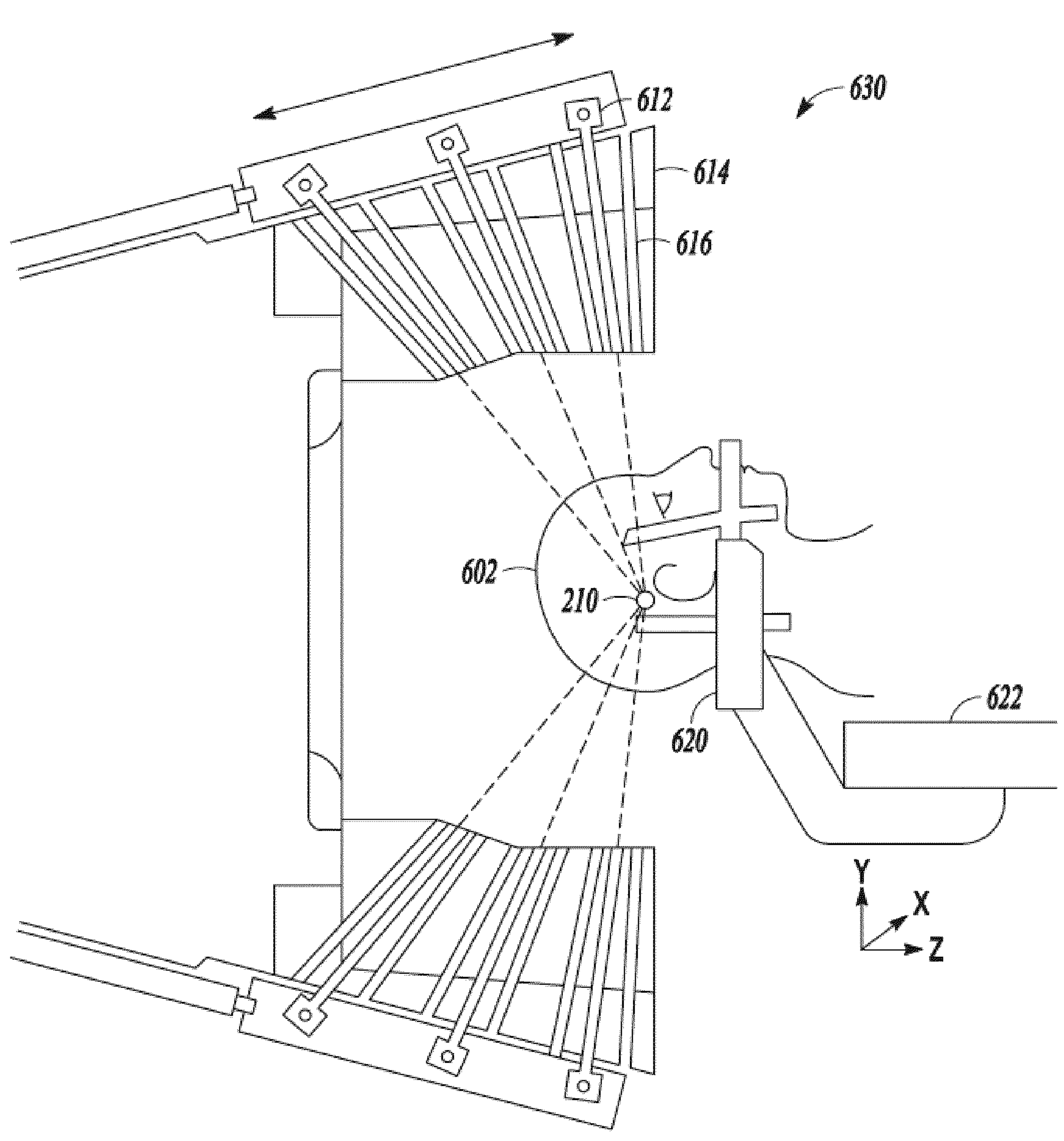
FIG. 6 illustrates an example Gamma Knife radiation therapy system, according to some embodiments of the present disclosure.

FIG. 6 illustrates an embodiment of another type of radiotherapy device 630 (e.g., a Leksell Gamma Knife), according to some embodiments of the present disclosure. As shown in FIG. 6, in a radiotherapy treatment session, a patient 602 may wear a coordinate frame 620 to keep stable the patient's body part (e.g., the head) undergoing surgery or radiotherapy. Coordinate frame 620 and a patient positioning system 622 may establish a spatial coordinate system, which may be used while imaging a patient or during radiation surgery. Radiotherapy device 630 may include a protective housing 614 to enclose a plurality of radiation sources 612.

Radiation sources 612 may generate a plurality of radiation beams (e.g., beamlets) through beam channels 616. The plurality of radiation beams may be configured to focus on an isocenter 210 from different directions. While each individual radiation beam may have a relatively low intensity, isocenter 210 may receive a relatively high level of radiation when multiple doses from different radiation beams accumulate at isocenter 210. In certain embodiments, isocenter 210 may correspond to a target under surgery or treatment, such as a tumor.

Figure 7A:
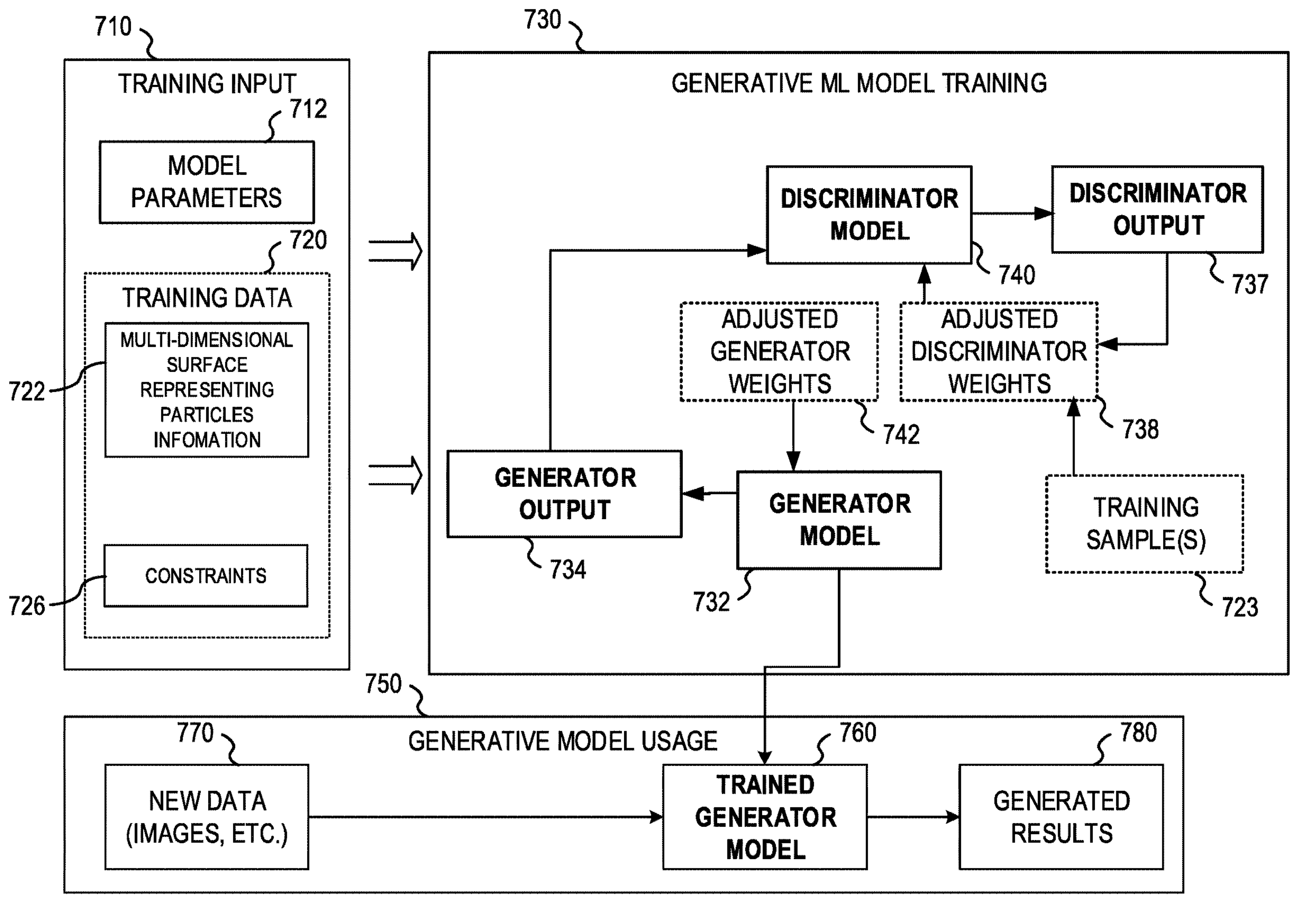
FIGS. 7A and 7B illustrate example flow diagrams for deep learning, according to some embodiments of the present disclosure.

FIG. 7A illustrates an example data flow for training and use of a GAN adapted for generating a synthetic samples of a phase space of a radiotherapy treatment device. For instance, the generator model 732 of FIG. 7A, which is trained to produce a trained generator model 760, may be trained to implement the processing functionality provided as part of the processor 114 in the radiotherapy system 100 of FIG. 1. Accordingly, a data flow of the GAN model usage 750 (prediction) is depicted in FIG. 7A as the provision of new data 770 (e.g., images or specified locations of a region of interest for a given patient or treatment device) to a trained generator model 760, and the use of the trained generator model 760 to produce a prediction or estimate of a generator output (samples of the phase space) 734 and/or generated results 780 (e.g., a simulation of dose at the specified locations or based on the images (new data 770) computed using the generated samples of the phase space (e.g., in accordance with the second phase of the Monte Carlo simulation).

GANs comprise two networks: a generative network (e.g., generator model 732) that is trained to produce an output (sample) 734 that tries to fool a discriminative network (e.g., discriminator model 740) that samples the generative network's output distribution (e.g., generator output (samples) 734) and decides whether that sample is the same or different from the true test distribution (obtained from training data 720, such as the multi-dimensional surface representing particles information 722 computed using a long form Monte Carlo simulation). The goal for this system of networks is to drive the generator network to learn the ground truth model or distribution of samples in the training data 720 as accurately as possible such that the discriminator network can only determine the correct origin for generator samples with 50% chance, which reaches an equilibrium with the generator network. The discriminator can access the ground truth, but the generator only accesses the training data through the response of the detector to the generator's output.

The data flow of FIG. 7A illustrates the receipt of training input 710, including various values of model parameters 712 and training data 720 and conditions or constraints 726. The training input 710 is provided to the GAN model training 730 to produce a trained generator model 760 used in the GAN model usage 750.

As part of the GAN model training 730, the generator model 732 is trained on real training samples of a phase space of a radiotherapy device (also depicted in FIG. 7B as 723), to produce samples of the phase space with a similar distribution. In this fashion, the generator model 732 is trained to produce, as generator output 734, simulated or synthetic samples of the phase space at random regions or specified regions of interest. The discriminator model 740 decides whether a simulated sample is from the training data (e.g., the training or true samples computed using the Monte Carlo simulation) or from the generator (e.g., the synthetic samples, as communicated between the generator model 732 and the discriminator model 740). The discriminator output 736 is a decision of the discriminator model 740 indicating whether the received sample is a simulated or real and is used to train the generator model 732. In some cases, the generator model 732 is trained utilizing the discriminator on the generated samples. This training process results in back-propagation of weight adjustments 738, 742 to improve the generator model 732 and the discriminator model 740.

During training of generator model 732, a batch of training data can be selected from the training data 720. The selected training data can include at least one sample from the phase space computed using the long form (first phase) of the Monte Carlo simulation. In detail, in a GAN model, the generator (e.g., generator model 732) learns a distribution over the data x, $p_G(x)$, starting with noise input with distribution $p_Z(z)$ as the generator learns a mapping $G(z;\theta_G):p_Z(z)\rightarrow p_G(x)$ where G is a differentiable function representing a neural network with layer weight and bias parameters $\theta_G$. The discriminator, $D(x;\theta_D)$ (e.g., discriminator model 740), maps the generator output to a binary scalar {true, false}, deciding true if the generator output is from actual data distribution $p_{data}(x)$ and false if from the generator distribution $p_G(x)$. That is, D(x) is the probability that xcame from $p_{data}(x)$ rather than from $p_G(x)$. In another embodiment, paired training data may be utilized in which, for instance, Y is conditioned (dependent) on X. In such cases, the GAN generator mapping is represented by $G(y|x;\theta_G):X\rightarrow Y$ from data domain X where data $x\in X$ represents the region of interest and domain Y where data $y\in Y$ represents the samples of the phase space corresponding to x.

Figure 7B:
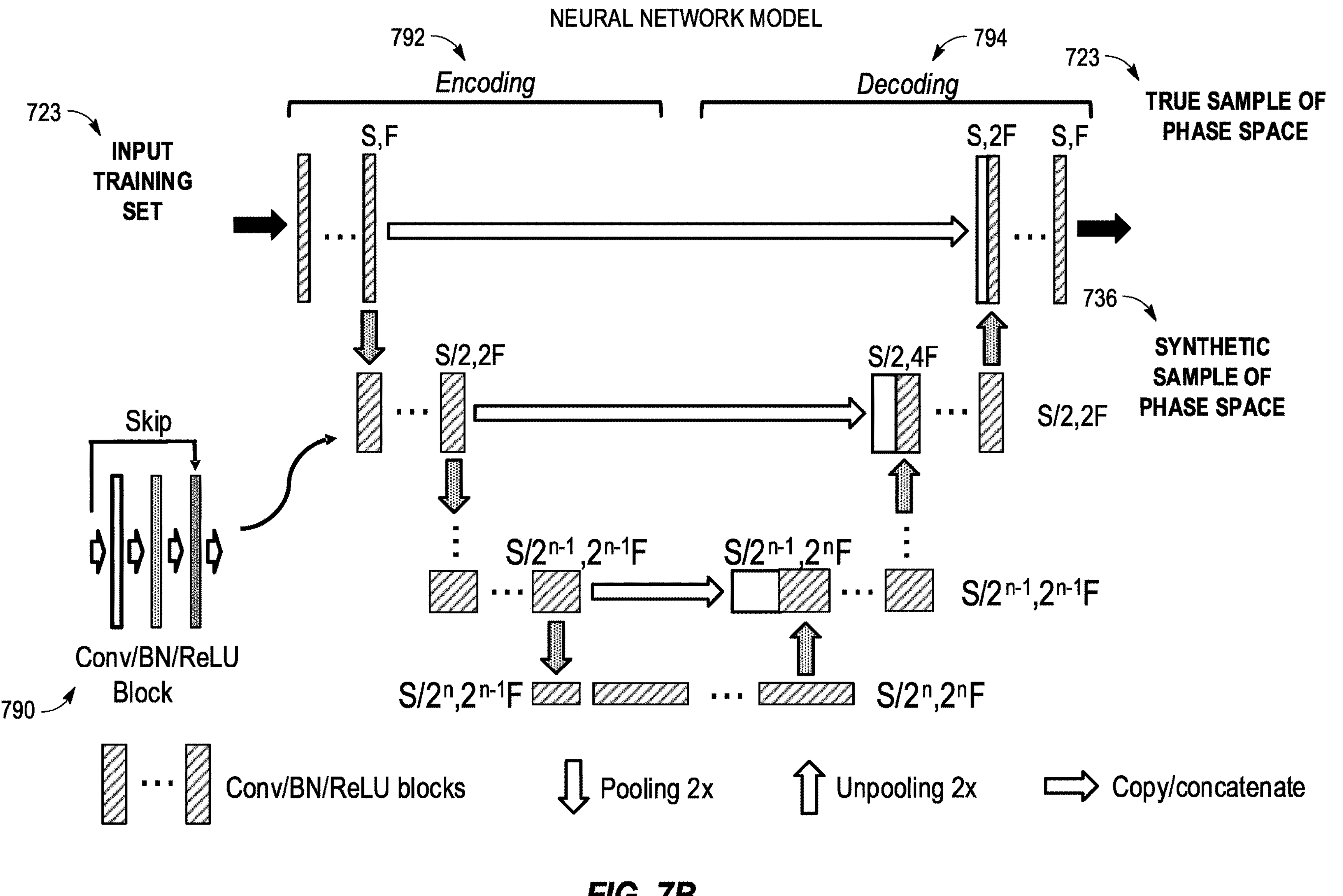

FIG. 7B illustrates an example convolutional neural network (CNN) model adapted for generating a sample of a phase space representation according to the present disclosure. Specifically, the model shown in FIG. 7B depicts an arrangement of a "U-Net" deep CNN designed for generating an output data set (output synthetic samples of the phase space) based on an input training set (e.g., samples of a phase space computed using the Monte Carlo simulation). The name derives from the "U" configuration, and as is well understood, this form of CNN model can produce pixel-wise classification or regression results. In some cases, a first path leading to the CNN model includes one or more deformable offset layers and one or more convolution layers including convolution, batch normalization, and an activation such as the rectified linear unit (ReLU) or one of its variants. The model generates as output data set synthetic samples of the phase space.

The left side of the model operations (the "encoding" operations 792) learns a set of features that the right side (the "decoding" operations 794) uses to reconstruct an output result. The U-Net has n levels consisting of conv/BN/ReLU (convolution/batch normalization/rectified linear units) blocks 790, and each block has a skip connection to implement residual learning. The block sizes are denoted in FIG. 7B by "S" and "F" numbers; input images are S×S in size, and the number of feature layers is equal to F. The output of each block is a pattern of feature responses in arrays the same size as the images.

Proceeding down the encoding path, the size of the blocks decreases by ½ or $2^{-1}$ at each level while the size of the features by convention increases by a factor of 2. The decoding side of the network goes back up in scale from $S/2^n$ while adding in feature content from the left side at the same level; this is the copy/concatenate data communication. The differences between the output image and the training version of that image drives the generator network weight adjustments by backpropagation. For inference, or testing, with use of the model, the input would be a region of interest of the phase space and the output would be synthetic samples of the phase space 736 for the region of interest.

In deep CNN training, the learned model is the values of layer node parameters θ (node weights and layer biases) determined during training. Training employs maximum likelihood or the cross entropy between the training data and the model distribution. A cost function expressing this relationship is $$\mathcal{L}(\theta) = -E_{x,y\sim p_{data}}\log p_{model}(y|x;\theta)$$

The exact form of the cost function for a specific problem depends on the nature of the model used. A Gaussian model $p_{model}(y|x)=N(y:f(x;\theta))$ implies a cost function such as:

$$\mathcal{L}(\theta) = -E_{x,y\sim p_{data}}\|y - f(x;\theta)\|_2^2 + const$$

which includes a constant term that does not depend on θ. Thus, minimizing $\mathcal{L}(\theta)$ generates the mapping f(x;θ) that approximates the training data distribution.

The representation of the model of FIG. 7B thus illustrates the training and prediction of a generative model, which is adapted to perform regression rather than classification.

Consistent with embodiments of the present disclosure, the treatment modeling methods, systems, devices, and/or processes based on such models include two stages: training of the generative model, with use of a discriminator/generator pair in a GAN; and prediction with the generative model, with use of a GAN-trained generator. It will be understood that other variations and combinations of the type of deep learning model and other neural-network processing approaches may also be implemented with the present techniques.

A useful extension of the GAN is the conditional GAN. Conditional adversarial networks learn a mapping from observed image x and random noise z as G:{x,z}=→y. Both adversarial networks consist of two networks: a discriminator (D) and a generator (G). The generator G is trained to produce outputs that cannot be distinguished from "real" or actual training samples of the phase space by an adversarially trained discriminator D that is trained to be maximally accurate at detecting "fakes" or outputs of G. The conditional GAN differs from the unconditional GAN in that both discriminator and generator inferences are conditioned on an example image of the type X.

The traditional GAN loss function is:

$$\mathcal{L}_{cGAN}(G,D) = \mathbb{E}_{y\sim p_{data}(y)}[\log(D(y))] + E_{z\sim p_z(z)}[\log(1-D(G(z)))]$$

The conditional GAN loss function is:

$$\mathcal{L}_{cGAN}(G,D) = \mathbb{E}_{x,y\sim p_{data}(x,y)}[\log(D(x,y))] + E_{x\sim p_{data}(x),z\sim p_z(z)}[\log(1-D(x,G(x,z)))]$$

where G tries to minimize this loss against an adversarial D that tries to maximize it, or, $$G^* = \arg\min_G \max_D \mathcal{L}_{cGAN}(G,D).$$

In addition, one wants the generator G to minimize the difference between the predicted samples of the phase space (or distribution of the phase space) and the actual training ground truth samples, $\mathcal{L}_{L1}(G)=\mathbb{E}_{x,y\sim p_{data}(x,y),z\sim p_z(z)}[\|y-G(x,z)\|_1]$ so the complete loss is the λ-weighted sum of two losses $$G^* = \arg\min_G \max_D \mathcal{L}_{cGAN}(G,D) + \lambda\mathcal{L}_{L1}(G).$$

The generator in the conditional GAN may be a U-Net.

According to some embodiments, the generator of the conditional GAN is trained to receive a selection of a region of interest and generates a synthetic sample of the phase space at that region of interest. The discriminator receives the synthetic sample from the generator and is trained to distinguish the received synthetic sample from being a real sample (computed by the Monte Carlo simulation and provided by the training data 720) or a fake or synthetic sample. The generator is trained to minimize a difference between the synthetic samples and the corresponding training samples of the phase space. To this end, after the generator generates the synthetic sample, the training sample corresponding to the region of interest in the phase space is retrieved. A comparison is made between the generated synthetic sample, and this retrieved training sample. Parameters of the generator are then updated based on the difference in an attempt to minimize the difference. The discriminator is similarly trained based on whether the discriminator correctly classifies the generated sample of the phase space as real or fake. The parameters of the generator are updated based on a total loss function that takes into account the discriminator errors and the generator differences.

Subsequently, a second sample for the same or different region of interest is retrieved. The generator receives this region of interest and generates a second synthetic sample of the phase space. A difference between the paired training sample and the synthetically generated sample is made and parameters of the generator are again updated based on this difference. Once all or a substantial portion of the training data is processed and used to update parameters of the generator and/or once a specified number of epochs or when the error (between synthetic samples and training samples) is within a threshold, the training ends and the generator's parameters are output.

In an embodiment, to begin network training, an iteration index can be set to an initial value of zero. A batch of training data can be formed from a subset of the received sets of samples of the phase space. The batch of training data can be provided to the GAN and the GAN parameters can be updated based thereon. In an embodiment, parameters of the GAN, Θ, can be updated, such as to minimize or reduce a cost function, such as the cost function $$\mathcal{L}(\Theta^* = \text{argmin}_\Theta \|Y - Y^*\|_2^2 + \lambda\|\Theta\|_1,$$

where Y can represent the samples of the phase space determined by the GAN, where Y* can represent the known distribution of samples of the phase space or samples of the phase space corresponding to the batch of training data, and where Θ* can represent parameters of the GAN (e.g., layer node weights and biases as described above) corresponding to a minimized square error between Y and Y*.

In an embodiment, the cost function can include a probabilistic function where parameters of the GAN can be determined according to the expression $\Theta_{train}=\text{argmax}_\Theta P(Y|X;\Theta)$, or $\Theta_{train}=\text{argmax}_\Theta \Sigma_{t\in T}\log P(Y_t|X_t;\Theta)$, where $\Theta_{train}$ can represent the parameters of the fully trained GAN, and X can represent a collection of samples at different regions of interest.

After updating the parameters of the GAN, the iteration index can be incremented by a value of one. The iteration index can correspond to a number of times that the parameters of the GAN have been updated. Stopping criteria can be computed, and if the stopping criteria are satisfied, then the GAN model can be saved in a memory, such as the memory device 116 of image processing device 112, and the training can be halted. If the stopping criteria are not satisfied, then the training can continue by obtaining another batch of training samples from the same region of interest or another region of interest. In an embodiment, the stopping criteria can include a value of the iteration index (e.g., the stopping criteria can include whether the iteration index is greater than or equal to a determined maximum number of iterations). In an embodiment, the stopping criteria can include an accuracy of the output distribution of the samples of the phase space provided by the generative model.

A motivation for predicting samples of the phase space, using a generative machine learning model (or neural network), is to accelerate treatment planning computations and dose simulations. Current, conventional treatment planning retrieves a phase space or computes a phase space using a Monte Carlo simulation. The retrieval and/or computation of the phase space consumes a great deal of resources and takes a very long time to load into memory of a processor. This slows down the ability to compute or simulate dose in a region of interest. The disclosed embodiments improve the quality and speed at which the treatment plans are created using a generative machine learning model that predicts the samples of the phase space. This avoids the need to load in real time the phase space from memory into a processor or the need to compute the phase space using a Monte Carlo simulation on the fly. This speeds up the second phase computation of the Monte Carlo simulation of simulating dose in a region of interest, which speeds up the planning process.

Figure 8:
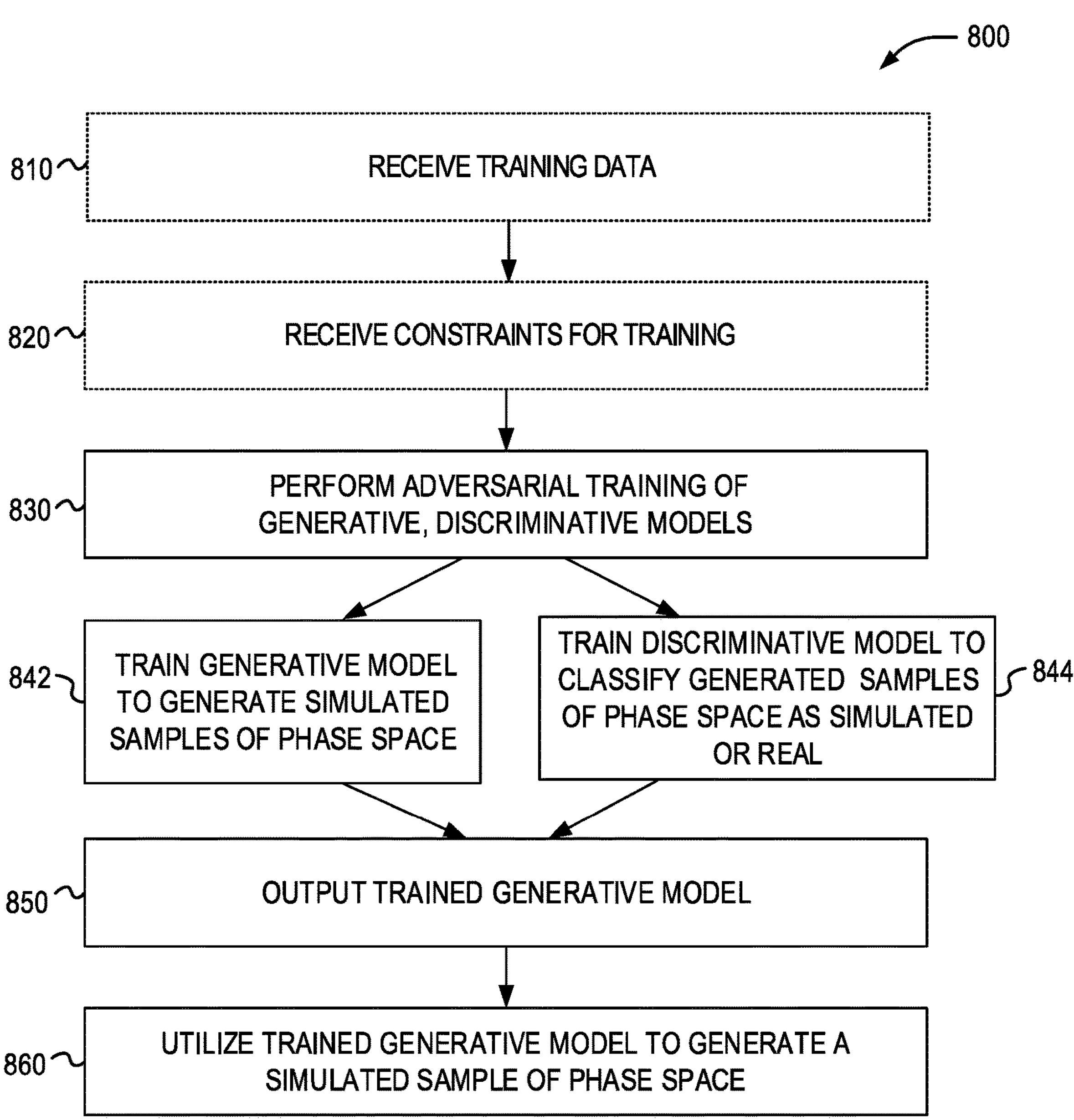
FIGS. 8 and 9 illustrate example data flows for training and use of a generative machine learning model to generate samples of a phase space according to some embodiments of the present disclosure.

FIG. 8 illustrates a flowchart of a process 800 of example operations for training a generative model adapted for outputting a synthetic collection samples of a phase space having a similar distribution as a phase space computed by a first phase of a Monte Carlo simulation. The process 800 is illustrated from the perspective of a radiotherapy system 100, which trains and utilizes a generative model using a GAN, as discussed in the preceding examples. However, corresponding operations may be performed by other devices or systems (including in offline training or verification settings separate from a particular image processing workflow or medical treatment).

As shown, a first phase of the flowchart workflow begins with operations (810, 820) to establish the parameters of training and model operations. The process 800 begins with operations to receive (e.g., obtain, extract, identify) training sample data (operation 810) and constraints or conditions for training (operation 820). In an example, this training sample data may comprise phase space samples computed by a long run of a Monte Carlo simulation. Also in an example, the constraints may relate to an imaging device, a treatment device, a patient, or medical treatment considerations. In an example, these constraints may include adversarial losses.

The second phase of the process 800 continues with training operations, including adversarial training of generative and discriminative models in a generative adversarial network (operation 830). In an example, the adversarial training includes training the generative model to generate simulated samples by processing an input collection of samples (operation 842). The collection of simulated samples is provided to a discriminative model to train the discriminative model to classify the generated simulated samples as simulated or real training data (operation 844). Also in this adversarial training, the output of the generative model is used for training the discriminative model, and the output of the discriminative model is used for training the generative model.

In various examples, the generative model and the discriminative model comprise respective convolutional neural networks.

The process 800 continues with the output of the generative model for use in generating a synthetic sample of the phase space (operation 850).

The process 800 continues with the utilization of the trained generative model to generate a simulated sample of the phase space. The simulated sample is used to simulate dose in a region of interest and ultimately to generate a radiotherapy treatment plan.

Figure 9:
Figure 9:
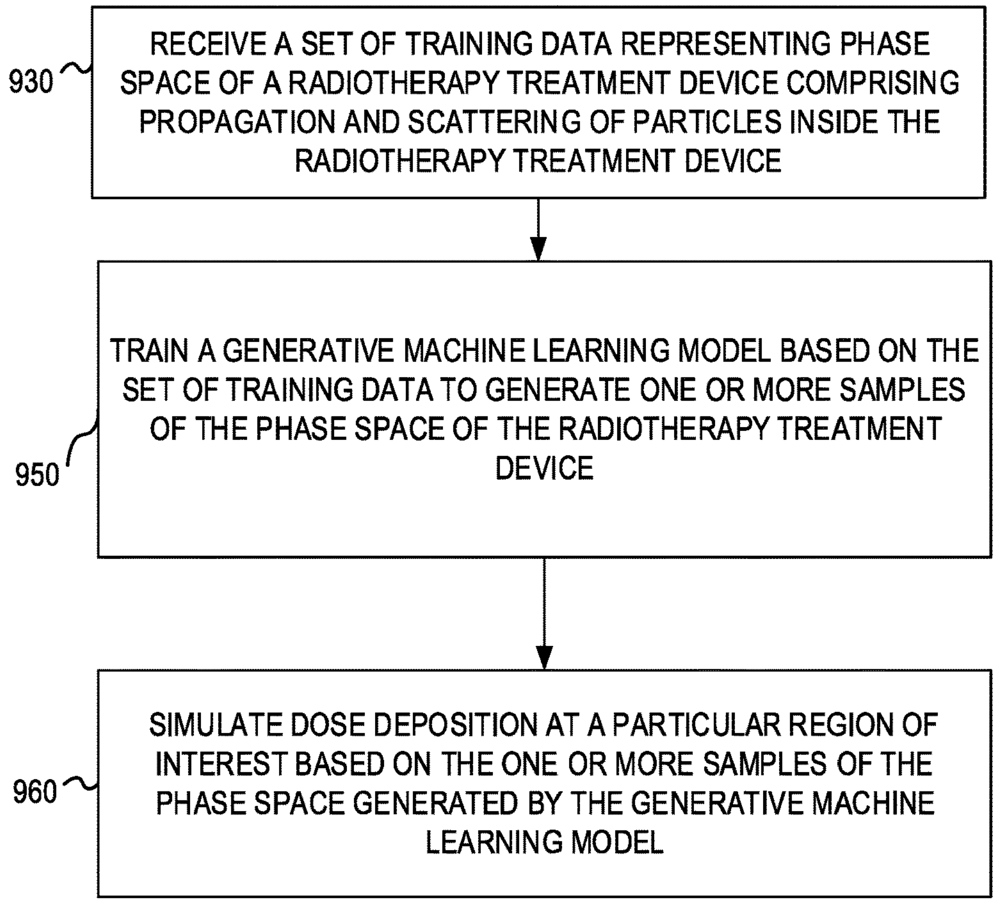

FIG. 9 is a flowchart illustrating example operations of the image processing device 112 in performing process 900, according to example embodiments. The process 900 may be embodied in computer-readable instructions for execution by one or more processors such that the operations of the process 900 may be performed in part or in whole by the functional components of the image processing device 112; accordingly, the process 900 is described below by way of example with reference thereto. However, in other embodiments, at least some of the operations of the process 900 may be deployed on various other hardware configurations. The process 900 is therefore not intended to be limited to the image processing device 112 and can be implemented in whole, or in part, by any other component. Some or all of the operations of process 900 can be in parallel, out of order, or entirely omitted.

At operation 930, image processing device 112 receives a set of training data representing phase space of a radiotherapy treatment device comprising propagation and scattering of particles inside the radiotherapy treatment device, as discussed above.

At operation 950, image processing device 112 trains a generative machine learning model based on the set of training data to generate one or more samples of the phase space of the radiotherapy treatment device, as discussed above.

At operation 960, image processing device 112 simulates dose deposition at a particular region of interest based on the one or more samples of the phase space generated by the generative machine learning model, as discussed above.

Figure 10:
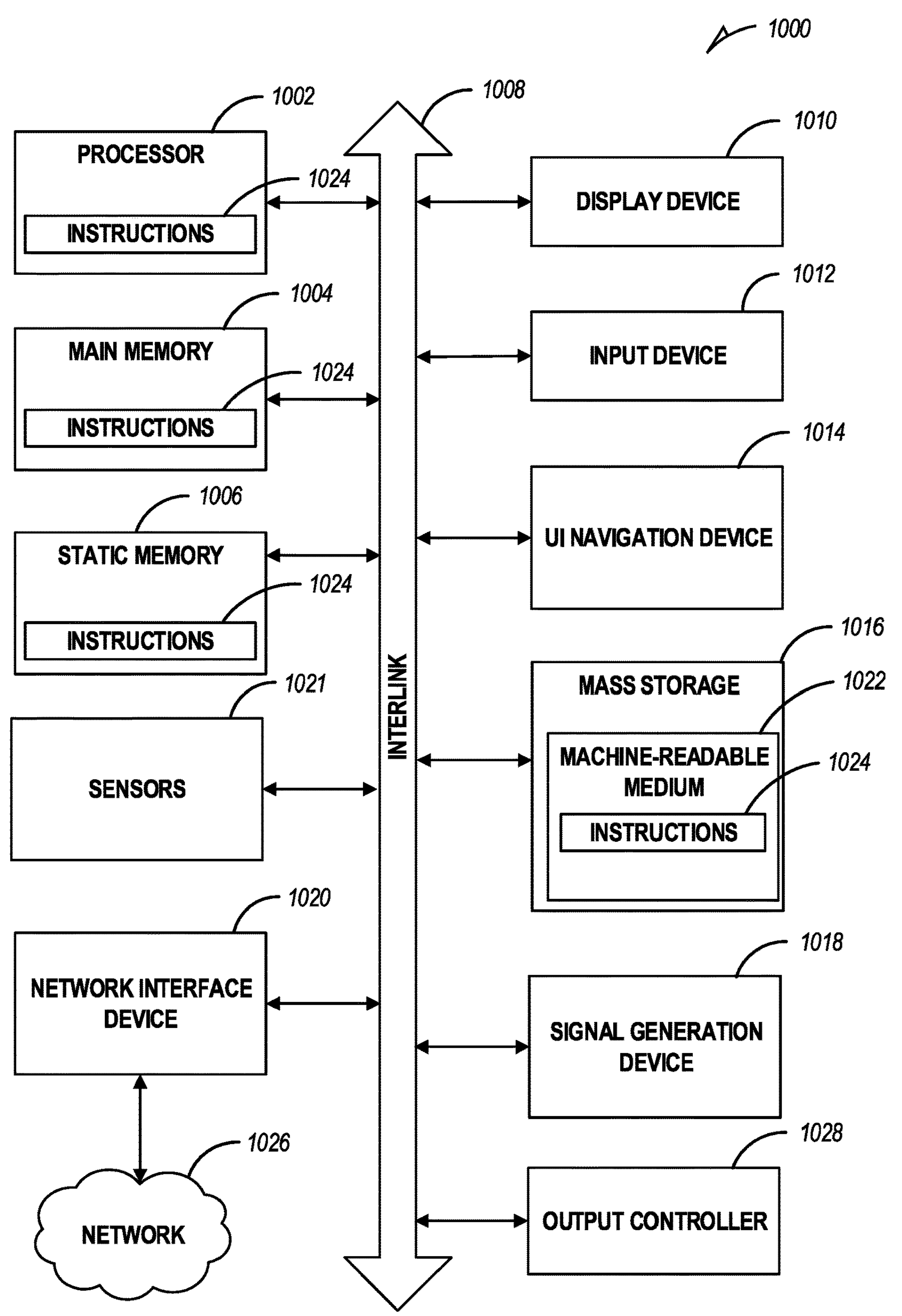
FIG. 10 illustrates an example block diagram of a machine on which one or more of the methods as discussed herein can be implemented.

FIG. 10 illustrates a block diagram of an embodiment of a machine 1000 on which one or more of the methods as discussed herein can be implemented. In one or more embodiments, one or more items of the image processing device 112 can be implemented by the machine 1000. In alternative embodiments, the machine 1000 operates as a standalone device or may be connected (e.g., networked) to other machines. In one or more embodiments, the image processing device 112 can include one or more of the items of the machine 1000. In a networked deployment, the machine 1000 may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 1000 includes processing circuitry or processor 1002 (e.g., a CPU, a graphics processing unit (GPU), an ASIC, circuitry, such as one or more transistors, resistors, capacitors, inductors, diodes, logic gates, multiplexers, buffers, modulators, demodulators, radios (e.g., transmit or receive radios or transceivers), sensors 1021 (e.g., a transducer that converts one form of energy (e.g., light, heat, electrical, mechanical, or other energy) to another form of energy), or the like, or a combination thereof), a main memory 1004 and a static memory 1006, which communicate with each other via a bus 1008. The machine 1000 (e.g., computer system) may further include a video display device 1010 (e.g., a liquid crystal display (LCD) or a cathode ray tube (CRT)). The machine 1000 also includes an alphanumeric input device 1012 (e.g., a keyboard), a user interface (UI) navigation device 1014 (e.g., a mouse), a disk drive or mass storage unit 1016, a signal generation device 1018 (e.g., a speaker), and a network interface device 1020.

The mass storage unit 1016 includes a machine-readable medium 1022 on which is stored one or more sets of instructions and data structures (e.g., software) 1024 embodying or utilized by any one or more of the methodologies or functions described herein. The instructions 1024 may also reside, completely or at least partially, within the main memory 1004 and/or within the processor 1002 during execution thereof by the machine 1000, the main memory 1004 and the processor 1002 also constituting machine-readable media.

The machine 1000 as illustrated includes an output controller 1028. The output controller 1028 manages data flow to/from the machine 1000. The output controller 1028 is sometimes called a device controller, with software that directly interacts with the output controller 1028 being called a device driver.

While the machine-readable medium 1022 is shown in an embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present disclosure, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), EEPROM, and flash memory devices; magnetic disks such as internal hard disks and removable disks; magneto-optical disks; and CD-ROM and DVD-ROM disks.

The instructions 1024 may further be transmitted or received over a communications network 1026 using a transmission medium. The instructions 1024 may be transmitted using the network interface device 1020 and any one of a number of well-known transfer protocols (e.g., HTTP). Examples of communication networks include a LAN, a WAN, the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

As used herein, "communicatively coupled between" means that the entities on either end of the coupling must communicate through an item therebetween and that those entities cannot communicate with each other without communicating through the item.

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," "third," and so forth, are used merely as labels and are not intended to impose numerical requirements on their objects.

Embodiments of the disclosure may be implemented with computer-executable instructions. The computer-executable instructions (e.g., software code) may be organized into one or more computer-executable components or modules. Aspects of the disclosure may be implemented with any number and organization of such components or modules. For example, aspects of the disclosure are not limited to the specific computer-executable instructions, or the specific components or modules illustrated in the figures and described herein. Other embodiments of the disclosure may include different computer-executable instructions or components having more or less functionality than illustrated and described herein.

Method examples (e.g., operations and functions) described herein can be machine or computer-implemented at least in part (e.g., implemented as software code or instructions). Some examples can include a computer-readable medium or machine-readable medium encoded with instructions operable to configure an electronic device to perform methods as described in the above examples. An implementation of such methods can include software code, such as microcode, assembly language code, a higher-level language code, or the like (e.g., "source code"). Such software code can include computer-readable instructions for performing various methods (e.g., "object" or "executable code"). The software code may form portions of computer program products. Software implementations of the embodiments described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media, CD-ROMS, magnetic-optical disks, removable optical disks (e.g., compact disks and digital video disks), flash memory devices, magnetic cassettes, memory cards or sticks (e.g., secure digital cards), RAMs (e.g., CMOS RAM and the like), recordable/non-recordable media (e.g., read only memories (ROMs)), EPROMS, EEPROMS, or any type of media suitable for storing electronic instructions, and the like. Such computer-readable storage medium is coupled to a computer system bus to be accessible by the processor and other parts of the OIS.

In an embodiment, the computer-readable storage medium may have encoded a data structure for treatment planning, wherein the treatment plan may be adaptive. The data structure for the computer-readable storage medium may be at least one of a Digital Imaging and Communications in Medicine (DICOM) format, an extended DICOM format, an XML format, and the like. DICOM is an international communications standard that defines the format used to transfer medical image-related data between various types of medical equipment. DICOM RT refers to the communication standards that are specific to radiation therapy.

In various embodiments of the disclosure, the method of creating a component or module can be implemented in software, hardware, or a combination thereof. The methods provided by various embodiments of the present disclosure, for example, can be implemented in software by using standard programming languages such as, for example, C, C++, Java, Python, and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general purpose computer selectively activated or reconfigured by a computer program stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved, and other advantageous results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. Many other embodiments will be apparent to those of skill in the art upon reviewing the above description. The scope of the disclosure should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

The Abstract is provided to comply with 37 C.F.R. § 1.72 (b), to allow the reader to quickly ascertain the nature of the technical disclosure. It is submitted with the understanding that it will not be used to interpret or limit the scope or meaning of the claims.

What is claimed is:

1. A computer-implemented method comprising:

receiving a set of training data representing a phase space of a radiotherapy treatment device comprising propagation and scattering of particles inside the radiotherapy treatment device;

training a generative machine learning model based on the set of training data to generate one or more samples of the phase space of the radiotherapy treatment device; and simulating a dose deposition at a particular region of interest based on the one or more samples of the phase space of the radiotherapy treatment device generated by the generative machine learning model, wherein a radiotherapy treatment plan for a patient is generated based on the simulated dose deposition.

2. The computer-implemented method of claim 1, wherein the set of training data describes position and momentum vectors of relevant particles within a set of regions of the radiotherapy treatment device.

3. The computer-implemented method of claim 1, wherein the generative machine learning model comprises a neural network comprising at least one of a generative adversarial network (GAN), a variational autoencoder (VAE), a normalizing flow network, or a diffusion model.

4. The computer-implemented method of claim 1, wherein the set of training data represent the phase space of the radiotherapy treatment device as a collection of samples from a probability distribution.

5. The computer-implemented method of claim 1, further comprising:

generating the set of training data by performing a Monte Carlo simulation, wherein the set of training data is stored and retrieved from a non-volatile storage device or is computed in real time.

6. The computer-implemented method of claim 1, wherein the set of training data comprises a multi-dimensional surface representing physical information about the particles inside the radiotherapy treatment device.

7. The computer-implemented method of claim 1, wherein the trained generative machine learning model is stored on a same processing device that simulates the dose deposition when simulating the dose deposition to avoid accessing the one or more samples of the phase space of the radiotherapy treatment device from a remote storage location.

8. The computer-implemented method of claim 1, further comprising:

generating a three-dimensional (3D) volume of the dose deposition based on an interaction between the one or more samples of the phase space of the radiotherapy treatment device and an image detector, and wherein the generative machine learning model is part of a radiotherapy system that includes the image detector.

9. The computer-implemented method of claim 1, further comprising:

generating a three-dimensional (3D) volume of the dose deposition based on an interaction between the one or more samples of the phase space of the radiotherapy treatment device and an image detector, and wherein the generative machine learning model is separate from a radiotherapy system that includes the image detector.

10. The computer-implemented method of claim 1, wherein:

the generative machine learning model comprises a generative adversarial network (GAN) configured to train a generative model using a discriminative model; and values applied by the generative model and the discriminative model are established using adversarial training between the discriminative model and the generative model.

11. The computer-implemented method of claim 10, wherein:

the adversarial training between the discriminative model and the generative model comprises:

training the generative model to generate a first synthetic sample of the phase space of the radiotherapy treatment device from a distribution of the particles inside the radiotherapy treatment device; and training the discriminative model to classify the first synthetic sample as a synthetic or a real training particle inside the radiotherapy treatment device; and an output of the generative model is used for training the discriminative model and an output of the discriminative model is used for training the generative model.

12. The computer-implemented method of claim 11, further comprising:

obtaining a particle from the set of training data; and computing a training loss for the discriminative model based on a result of comparing an output of the discriminative model with the particle obtained from the set of training data.

13. The computer-implemented method of claim 11, wherein the first synthetic sample is generated based on a random point within the phase space or a specified region within the phase space.

14. The computer-implemented method of claim 1, wherein the generative machine learning model comprises a normalizing flow network, further comprising:

obtaining a particle from the set of training data;

computing a training loss based on a likelihood of the particle obtained from the set of training data based on a distribution provided by the normalizing flow network; and updating the distribution provided by the normalizing flow network based on the training loss.

15. The computer-implemented method of claim 14, further comprising:

computing a new particle based on a distribution provided by the normalizing flow network, wherein the new particle is computed based on a random point within the phase space or a specified region within the phase space of the radiotherapy treatment device.

16. A system for generating one or more radiotherapy treatment plans, the system comprising:

one or more processors configured to perform operations comprising:

receiving a set of training data representing a phase space of a radiotherapy treatment device comprising propagation and scattering of particles inside the radiotherapy treatment device;

training a generative machine learning model based on the set of training data to generate one or more samples of the phase space of the radiotherapy treatment device; and simulating a dose deposition at a particular region of interest based on the one or more samples of the phase space of the radiotherapy treatment device generated by the generative machine learning model, wherein a radiotherapy treatment plan for a patient is generated based on the simulated dose deposition.

17. The system of claim 16, wherein the set of training data describes position and momentum vectors of relevant particles within a set of regions of the radiotherapy treatment device.

18. The system of claim 16, wherein the generative machine learning model comprises a neural network comprising at least one of a generative adversarial network (GAN), a variational autoencoder (VAE), a normalizing flow network, or a diffusion model.

19. A non-transitory computer-readable medium comprising non-transitory computer-readable instructions for performing operations of claim 1.

20. A computer-implemented method comprising:

accessing a generative machine learning model that has been trained based on a set of training data to generate one or more samples of a phase space of a radiotherapy treatment device, the set of training data comprising propagation and scattering of particles inside the radiotherapy treatment device; and simulating a dose deposition at a particular region of interest based on the one or more samples of the phase space of the radiotherapy treatment device generated by the generative machine learning model, wherein a radiotherapy treatment plan for a patient is generated based on the simulated dose deposition.

21. The computer-implemented method of claim 20, wherein the set of training data describes position and momentum vectors of relevant particles within a set of regions of the radiotherapy treatment device.

22. The computer-implemented method of claim 20, wherein:

the generative machine learning model comprises a generative adversarial network (GAN) configured to train a generative model using a discriminative model; and values applied by the generative model and the discriminative model are established using adversarial training between the discriminative model and the generative model.

23. The computer-implemented method of claim 22, wherein:

the adversarial training between the discriminative model and the generative model comprises:

training the generative model to generate a first synthetic sample of the phase space of the radiotherapy treatment device from a distribution of the particles inside the radiotherapy treatment device; and training the discriminative model to classify the first synthetic sample as a synthetic or a real training particle inside the radiotherapy treatment device; and an output of the generative model is used for training the discriminative model and an output of the discriminative model is used for training the generative model.

* * * * *